US010350298B2

(12) United States Patent
Rowan et al.

(10) Patent No.: US 10,350,298 B2
(45) Date of Patent: Jul. 16, 2019

(54) IMMUNOMODULATORY PROTEIN CONSTRUCTS WITH A HELICAL POLYMERIC BACKBONE

(75) Inventors: Alan Edward Rowan, Nijmegen (NL); Carl Gustav Figdor, Nijmegen (NL)

(73) Assignees: Stichting Katholieke Universiteit, Radboud University Nijmegen Medical Centre, Nijmegen (NL); Stichting Katholieke Universiteit, meer in het bijzonder Radboud Universiteit Nijmegen, Nijmegen (NL)

( * ) Notice: Subject to any disclaimer, the term of this patent is extended or adjusted under 35 U.S.C. 154(b) by 1141 days.

(21) Appl. No.: 13/808,897

(22) PCT Filed: Jul. 7, 2011

(86) PCT No.: PCT/EP2011/061559
§ 371 (c)(1),
(2), (4) Date: Apr. 22, 2013

(87) PCT Pub. No.: WO2012/004369
PCT Pub. Date: Jan. 12, 2012

(65) Prior Publication Data
US 2013/0202548 A1 Aug. 8, 2013

Related U.S. Application Data

(60) Provisional application No. 61/399,180, filed on Jul. 7, 2010.

(30) Foreign Application Priority Data

Jul. 7, 2010 (EP) ..................................... 10168747

(51) Int. Cl.
*A61K 47/64* (2017.01)
*A61K 47/59* (2017.01)
*A61K 47/48* (2006.01)
*A61K 47/60* (2017.01)
*C07K 14/74* (2006.01)

(52) U.S. Cl.
CPC ........ *A61K 47/48192* (2013.01); *A61K 47/59* (2017.08); *A61K 47/60* (2017.08); *A61K 47/646* (2017.08)

(58) Field of Classification Search
None
See application file for complete search history.

(56) References Cited

FOREIGN PATENT DOCUMENTS

| WO | WO 97/46256 | 12/1997 |
|----|----|----|
| WO | WO 02/072631 A2 | 9/2002 |
| WO | WO 05/028505 | 3/2005 |
| WO | WO 2006/083874 A2 | 8/2006 |
| WO | WO 2008/116468 A2 | 10/2008 |
| WO | WO 2009/003492 A1 | 1/2009 |
| WO | WO 2009/094273 A2 | 7/2009 |
| WO | WO 2011/007012 | 1/2011 |
| WO | WO 2012/004369 | 1/2012 |

OTHER PUBLICATIONS

Klebanoff et al (Immunol. Rev. 2011, 239: 27-44).*
Schrieber et al (Seminar. Immunol. 22: 105-112, 2010).*
Fournier and Schirrmacher (Expert. Rev. Vaccines 8(1); 51-66).*
Tsoukas et al (J. Immunol. 1985, 135: 1719-1723).*
Kimachi et al (Eur. J. Immunol. 1997, 27: 3310-3317) (Year: 1997).*
Boesteanu and Katsikis (Seminars in Immunology, 2009 21: 69-77).*
PCT International Preliminary Report on Patentability for PCT/EP2011/061559, dated Jan. 8, 2013.
Steenblock et al., A Comprehensive Platform for Ex Vivo T-cell Expansion Based on Biodegradable Polymeric Artificial Antigen-presenting Cells, XP-002551496 The American Society of Gene Therapy, Apr. 2008, pp. 765-772, vol. 16, No. 4.
Gac et al., Cysteine-Containing Polyisocyanides as Versatile Nanoplatforms for Chromophoric and Bioscaffolding, XP-002660898 Chemistry a European Journal, Jun. 1, 2010, pp. 6176-6186, 16.
Steenblock et al., Antigen presentation on artificial acellular substrates: modular system for flexible, adaptable immunotherapy, XP009124553 Expert Opinion, Oct. 21, 2009, pp. 451-464.
Kitto et al., Post-modification of helical dipeptido polyisocyanides using the 'click' reaction, XP009126768 Journal of Materials Chemistry, Oct. 22, 2008, pp. 5615-5624, 18.
Written Opinion PCT/EP2011/061559 dated Jul. 7, 2011.
PCT International Search Report, PCT/EP2011/059959, dated Nov. 29, 2011.

* cited by examiner

*Primary Examiner* — G. R. Ewoldt
*Assistant Examiner* — Marianne Dibrino
(74) *Attorney, Agent, or Firm* — Patent Law Works LLP

(57) ABSTRACT

The present invention relates to protein constructs that comprise one or more peptides, proteins, factors, compounds or other components as further described herein that are linked to and/or are linked to each other via a helical polymeric backbone. The constructs of the invention are suitable for administration to a human or animal body and can be used for pharmaceutical purposes, for example, for immunotherapy, such as for treating cancer and for other immunological applications, as well as for other therapeutic, prophylactic and/or diagnostic purposes.

18 Claims, 11 Drawing Sheets

4B

4A

IMMUNOMODULATORY PROTEIN CONSTRUCTS WITH A HELICAL POLYMERIC BACKBONE

CROSS-REFERENCE TO RELATED APPLICATIONS

This application is a national phase entry under 35 U.S.C. § 371 of International Patent Application PCT/EP2011/061559, filed Jul. 7, 2011, designating the United States of America and published in English as International Patent Publication WO 2012/004369 A1 on Jan. 12, 2012, which claims the benefit under Article 8 of the Patent Cooperation Treaty and under 35 U.S.C. § 119(e) to U.S. Provisional Patent Application Ser. No. 61/399,180, filed Jul. 7, 2010, and to European Patent Application Serial No. 10168747.3, filed Jul. 7, 2010, the disclosure of each of which is hereby incorporated herein by this reference in its entirety.

TECHNICAL FIELD

The present invention relates to protein constructs that comprise one or more peptides, proteins, factors, compounds or other components (as further described herein) that are linked to (and are linked to each other via) a helical polymeric backbone (also as described herein). As further described herein, the constructs of the invention are suitable for administration to a human or animal body and can be used for pharmaceutical purposes, for example, for immunotherapy (for example, of cancer) and for other immunological applications, as well as for other therapeutic, prophylactic and/or diagnostic purposes.

BACKGROUND

In one specific aspect, the invention provides such constructs that can be used as "artificial" or "synthetic" antigen-presenting cells (for example, as "artificial" or "synthetic" dendritic cells). In this aspect, the constructs of the invention can, in particular, be used to present one or more antigens to one or more T-cells (either in vitro, ex vivo or in vivo); to activate, to inhibit and/or to modulate (one or more immunological activities of) one or more T-cells and/or to otherwise interact with one or more T-cells (again, either in vitro, ex vivo or in vivo); and/or other cells of the immune system that recognize specific antigens such as B-cells or NKT-cells or NK-cells; and/or generally to induce and/or to enhance an immune response against a desired antigen in a subject to be treated (or alternatively, to suppress such an immune response, as further described herein). Again, in this aspect, the constructs of the invention can be used for immunotherapy (for example, of cancer) and for other immunological applications, as further described herein.

The invention further relates to methods for preparing the constructs described herein, to pharmaceutical compositions that contain one or more constructs of the invention, to applications and uses of such constructs and of such compositions, and also to the use of a pharmaceutically acceptable helical polymer (as further described herein) in preparing the constructs of the invention.

Other aspects, embodiments, features, applications, uses and advantages of the invention will become clear from the further description herein.

Generally, unless explicitly defined otherwise herein, the terms used in this specification have their usual meaning in the art (being the art of immunology for all immunological terms, the art of protein chemistry for all terms relating to protein manipulation and chemistry, and the art of polymer science for all terms relating to the description and manufacture of polymers), for which reference is made to the handbooks and review articles cited herein. Also, all methods and techniques that are not described in detail in the present application can be performed using standard techniques in the field of immunology, protein chemistry or polymer science, respectively, for which reference is again made to the handbooks and review articles cited herein.

Also, generally, the constructs of the invention that contain a pharmaceutically acceptable helical polymeric carrier (as described herein) and one or more (and usually two or more) proteins, peptides, factors, subunits, binding units or other compounds or biological moieties (also as described herein) will also be referred to herein as "constructs of the invention." The proteins, peptides, factors, subunits, binding units or other compounds or biological moieties that may be present in the constructs of the invention are also collectively referred to herein as "components" of the constructs of the invention. The pharmaceutically acceptable helical polymer that is present in the constructs of the invention is also referred to herein as the "polymeric backbone."

Immunotherapy can generally be described as the treatment of a disease by inducing, enhancing or suppressing an immune response, e.g., in a subject to be treated. Generally, the active agents used in immunotherapy are referred to as "immunomodulators" or having an "immunomodulatory" action or effect. Reference is, for example, made to the following handbooks and review articles: Parham, *The Immune System*, 3rd edition, Taylor and Francis, 2009; *Roitt's Essential Immunology*, 11 th Edition, Peter Delves (University College London), Seamus Martin (Trinity College, Dublin), Dennis Burton (The Scripps Research Institute, CA), Ivan Roitt (Royal Free & University College Medical School); *Janeway's Immunobiology*, Seventh Edition, Kenneth M. Murphy, Paul Travers, Mark Walport, as well as the further references cited therein.

For example, despite significant advances in conventional therapies (surgical procedures, chemotherapy and radiotherapy), the prognosis for multiple types of cancer remains low and recurrent disease often develops in advanced-stage cancer patients. Anti-cancer immunotherapy represents a promising strategy, as it is designed to specifically activate the immune system to eradicate tumor cells. The importance of the immune system in controlling tumor growth is demonstrated by the higher survival of patients with intratumoral T-cells compared to patients without intratumoral T-cells (Zhang et al., *N. Engl. J. Med.* (2003) 348:203-213).

One form of immunotherapy involves the use of dendritic cells or "DCs" (or other suitable antigen-presenting cells or "APCs") that have been modified (for example, loaded with an antigen against which an immune response is to be raised) so as to allow them to achieve a desired immunological or biological effect (for example, raising or enhancing an immune response against a desired antigen, such as an antigen that is expressed by a tumor to be treated), often via the naturally occurring antigen-presenting interaction between the APCs and T-cells, which, in turn, leads to activation of the T-cells and to an immune response against the antigen.

Very generally, this interaction between APCs and T-cells can be said to be primarily mediated by the interaction of a major histocompatibility complex or "MHC" (which presents the antigen to the T-cells in the form of an MHC-antigen complex) on the surface of the APC and a T-cell receptor or "TCR" on a T-cell. However, it is also well known that a number of other co-stimulatory factors, signals and interactions (such as the interaction between CD80/CD86 on APCs with CD28/CTLA-4 on T-cells) and other immunomodulatory peptides and factors (such as, for example, cytokines and chemokines) also play an important role in the interaction between APCs and T-cells (and, more generally, in activating, enhancing or modulating T-cell activity and/or immune responses against an antigen), often working as a "second signal" to the T-cell. The term MHC in this context is herein defined as molecules capable of presenting antigen to T-cells.

It will also immediately be clear to the skilled person that these interactions between the MHC-antigen complex on the APC and the TCR on the T-cell, as well as the interaction between co-stimulatory factors on APCs and their receptors on a T-cell, are just two of the more important interactions between APCs and T-cells, and generally form part of a larger complex of signaling, factors and interactions that are involved in antigen presentation, in the interaction between APCs and T-cells generally, in T-cell activation/modulation and/or in raising an immune response against an antigen. For a detailed description of the same, reference is, for example, made to the handbooks and review articles mentioned above in the paragraph on immunotherapy as well as the further references cited therein. Reference is, for example, also made to Huppa et al., *Nature* (2010) 463:963-967.

Similarly, it is known that APCs can stimulate natural killer T-cells ("NKT cells"), a group of T-cells that share properties of both T-cells and natural killer cells, but that recognize lipid and glycolipid antigens (presented by CD1d molecules) rather than peptide antigens presented by MHC complexes (see, for example, Melián et al., *Curr. Opin. Immunol.* 8(1):82-8 (1996); Brigl and Brenner, *Annu. Rev. Immunol.* 22:817-90 (2004); and Martin et al., *Proc. Natl. Acad. Sci. U.S.A.* 83(23):9154-8 (1987).

For a further description of the use of DCs in immunotherapy, reference is made to the following handbooks and review articles: "Dendritic cell immunotherapy: mapping the way," Carl G Figdor et al., *Nature Medicine* 10:475-480 (2004); and "Taking dendritic cells into medicine," Steinman and Banchereau, *Nature* (2007), Sep. 27, 449(7161): 419-26, as well as the further references cited therein.

The use of live DCs in immunotherapy (or generally in raising or modulating an immune response in a subject), although highly successful as therapy, has a number of practical disadvantages, the main one being that live DCs have to be harvested from the subject and/or differentiated in vitro from precursor in order to be loaded, ex vivo, with the desired antigen(s) and then have to be placed back into the subject. Apart from also being cumbersome and expensive because of the extensive safety requirements (GMP/GLP), these techniques also have the usual limitations that are associated with working with living cells, such as limitations as to time (depending on how long the DCs can be kept viable outside the body of the subject) and as to scale (which can generally be said to be limited to laboratory scale without major scale-up being feasible); and also are subject to the variability that is inherent when working with living systems. Furthermore, whereas live DCs need to be autologous due to HLA restriction and host-versus-graft rejection, synthetic APCs are applicable to every patient.

For this reason, the art has been looking for alternatives to the use of live DCs in immunotherapy. One such alternative involves the use of "artificial" or "synthetic" DCs, i.e., protein-based constructs that are designed to mimic one or more of the properties and immunological effects of DCs, in particular, when it comes to presenting antigens to T-cells and/or to inducing or stimulating T-cells. Generally, such artificial antigen-presenting cells comprise a suitable carrier (for example, spherical-shaped structures such as magnetic beads, latex beads or poly(lactic-co-glycolic acid) (PLGA) microparticles) to which are attached one or more proteins, peptides or factors that can, for example, present antigen to T-cells (such as suitable MHC-antigen complexes), that can induce or stimulate T-cells (such as co-stimulatory factors, for example, those naturally occurring on APCs), and/or that can generally improve or enhance the binding and/or interaction between the synthetic APCs and T-cells and/or provide a desired immunomodulatory effect. Reference is, for example, made to Steenblock et al., *Expert Opin. Biol. Ther.* (2009) 9:451-464; Chang, *Exp. Mol. Med.* (2006) 38:591-598; Lu et al., *Cancer Immunol. Immunother.* (2009) 58:629-638; Oelke et al., *Nat. Med.* (2003) 9:619-624; and Zhang et al., *J. Immunol.* (2007) 179:4910-4918; J. Greensmith and U. Aickelin (2009), "Artificial Dendritic Cells Multi-faceted Perspectives" (PDF), in *Human-Centric Information Processing Through Granular Modelling:* 375-395; Steenblock et al. *Molecular Therapy* (2008) 16(4):765-772; Chang et al. *Experimental and Molecular Medicine* (2006) 38(6):591-598; Maus et al., *Clinical Immunology* (2003) 106:16-22; Rudolf et al., *Cancer Immunol. Immunother.* (2008) 57:175-183; Goldberg et al., *The Journal of Immunology* (2003) 170:228-235; Caserta et al., *Cancer Research* (2008) 68(8):3010-3018, as well as to, for example, to U.S. Pat. No. 6,787,154.

DISCLOSURE

Generally, it is an objective of the invention to provide a new class of "artificial" or "synthetic" APCs that are an alternative (and preferably an improved alternative) compared to the synthetic/artificial APCs that have been described in the art (and, in particular, those that are based on a spherical and/or particulate carrier).

In its broadest sense, the invention achieves this by providing, for the purposes set out herein, a pharmaceutically acceptable carrier that can be used, with the advantages set out herein, in the preparation of artificial antigen-presenting cells and, more generally, as a pharmaceutically acceptable carrier to which various proteins, peptides, factors and/or other compounds (for example, as further described herein) can be easily linked (e.g., covalently using standard techniques of protein chemistry) in order to provide a pharmaceutically acceptable protein construct with pre-determined and/or "tailor-made" immunomodulatory properties. In the constructs of the invention, these proteins, peptides, factors and other compounds are linked to (and are linked to each other via) the carrier.

The invention also provides artificial antigen-presenting cells that comprise such a carrier (and one or more further components as described herein), and more generally protein or peptide constructs in which two or more proteins, peptides, factors and/or other components (as described herein) are linked to (and are linked to each other via) the carrier.

As further described herein, in the invention, the objectives and advantages set out herein are generally achieved by using a filamentous or "worm-like" polymer (as further described herein) as the carrier to which the various proteins, peptides, factors and/or other components that are present in the constructs of the invention are linked (or in other words, essentially by linking the proteins, peptides, factors and/or other components present in the constructs of the invention to each other by means of a filamentous polymer as further described herein).

Generally, the filamentous or "worm-like" polymer as used herein can be described as a polymer that, when present in an aqueous medium (such as a physiological salt solution, a culture medium for human or other mammalian cells, or another aqueous fluid or medium that is representative for physiological conditions), retains a "filamentous" or "worm-like" structure (rather than rolling itself up into a "polymer ball"). This can, for example, be determined using confocal microscopy techniques known per se.

In particular, the filamentous polymer used in the invention can essentially consist of filaments with a length of less than 75 micrometers and, in particular, between 0.01 and 50 micrometers, more, in particular, between 0.05 and 25 micrometers, such as between 0.1 and 10 micrometers, for example, between 0.5 and 5 micrometers, which retain a "filamentous" or "worm-like" form/conformation in a physiological aqueous medium when observed by confocal microscopy.

When the present description or claims refer to the "length" of the filaments used as carrier, it will be clear to the skilled person that often, the length of the filaments used will not be the same for all individual filaments and may have a statistical distribution. Thus, when it is said that the filamentous polymer used in the invention can consist of filaments with lengths between "x" and "y" micrometers (for example, between 0.01 and 50 micrometers, more, in particular, between 0.05 and 25 micrometers, such as between 0.1 and 10 micrometers, for example, between 0.5 and 5 micrometers, as mentioned in the previous paragraph) that at least 90%, preferably at least 95% and, more preferably, at least 99% of all individual filaments have a length between "x" and "y" micrometers. In this respect, it should be noted that generally, the longer that the polyisocyanide filaments are, usually the larger the polydispersity is (data not shown). Thus, when producing filaments of short length, the polydispersity will be smaller than when producing polyisocyanides of long length.

These lengths are well below the length of 75 micrometers, which is generally considered to be a length above which polymeric fibers or strands become unsuitable for administration to human beings.

Typically, the filaments used in the invention will be around 50 nm to 3000 nm long.

In the invention, the filamentous polymer used may, in particular, be a helical polymer. A helical polymer can generally be described as a polymer that, through intermolecular interactions (such as intermolecular hydrogen bonds), is capable of assuming an essentially helical structure when dissolved in water (and/or in another aqueous solution or medium or in a physiological fluid, such as a physiological buffer, physiological salt solution, blood, plasma, lymph fluid or another body fluid, or a suitable aqueous medium for culturing human or mammalian cells). Polymers of this type are also referred to in the art of polymer chemistry as "helical polymers." Reference is, for example, made in the reviews by Nolte, *Chem. Soc. Rev.* (1994) 23(1):11-19; Yashima et al., *Chem. Rev.* (2009) 109(11):6102-6211; Kumaki et al., *Chem. Rev.* (2009) 109 (11):6102-6211; Furusho and Yashima, *J. Polym. Sci., Part A: Polym. Chem.* (2009) 47:5195; as well as, for example, to Hase et al. *E. Chem.—Asian J.* (2007) 2:755-763; Kitto et al., *J. Mater. Chem.* (2008) 18:5615-5624; Roks et al., *Macromolecules* (1992) 25:5398-5407; Suginome and Ito, *Adv. Polym. Sci.* (2004), 171:77-136; Green et al., *Science* 30 Jun. 1995: Vol. 268. no. 5219, pp. 1860-1866; Cornelissen et al., *Science* 27 Jul. 2001, Vol. 293. no. 5530, pp. 676-680; Schwartz et al., *J. Mater. Chem.* 17, 19:1876-1884 (2007); Metselaar et al., *J. Pol. Sci., Part A: Polym. Chem.* 45:981-988 (2007); Wezenberg et al., *Chem. Eur. J.* 12, 10:2778-2786 (2006); Metselaar et al., *Angewandte Chemie International Edition* 117, 2026-2029 (2005); De Witte et al., *Chemistry: A European Journal*, 9, 8:1775-1781 (2003); Cornelissen et al., *Macromolecular Chemistry and Physics* 203, 10-11, 1625-1630 (2002); Cornelissen et al., *Journal of Polymer Science, Part A, Polymer Chemistry* 39, 24, 4255-4264 (2001); and Cornelissen et al., *Science* 293, 5530, 676-680 (2001).

These references also generally describe different kinds of helical polymers (see, for example, the review by Nolte, page 11, left hand column, who mentions polymers of isocyanides, poly(choral) and poly(methacrylate esters) and the types of backbones and (intermolecular) interactions (in particular, but without limitation, between side chains) that allow helical polymers to assume and maintain a helical confirmation in solution. These references further describe methods (monomers, catalysts, reaction conditions, etc.) that can generally be used for the preparation of helical polymers, as well as methods for determining the conformation and structure of helical polymers (such as circular dichroism spectroscopy techniques). These references also describe some of the applications and uses that have been suggested in the art for helical polymers.

Reference is also made to the non-prepublished priority patent application EP09165705 filed on Jul. 16, 2009, entitled "Method for the preparation of high molecular weight oligo(alkylene glycol) functionalized polyisocyanopeptides" by applicant (Rowan, Alan Edward, inventor), which also describes a helical polyisocyanide polymer useful in the practice of the present invention. This application is published on Jan. 20, 2011 as WO 2011/007012 and is hereby and herein incorporated by reference.

It is described therein that oligo(alkylene glycol) functionalized polyisocyanopeptide polymers may be synthesized in a new way starting from isocyanopeptide monomers functionalized with oligo-(alkylene glycol) side chains. This yields polymers with the required stiffness for use in the present invention. When oligo(alkylene glycol) functionalized polyisocyanopeptide polymers are synthesized in the conventional way (such as described in Kitto et al., *J. Materials Chemistry* (2008) 18:5615-5624) the functionalization with oligo-alkylene glycol occurs after the polymerization, resulting in polymers without the required stiffness. Such conventional polymers will, therefore, perform less, if at all, in the present invention.

Oligo(alkylene glycol) functionalized polyisocyanopeptide polymers prepared according to the method described in WO 2011/007012 are, therefore, distinguishable from conventional oligo(alkylene glycol) functionalized polyisocyanopeptide polymers with respect to their stiffness. Oligo (alkylene glycol) functionalized polyisocyanopeptide polymers prepared according to the method disclosed in WO2011/007012 are herein referred to as homopolymers.

In other words, homopolymers are oligo(alkylene glycol) functionalized polyisocyanopeptides obtained by a method comprising the steps of functionalizing an isocyanopeptide with oligo-(alkylene glycol) side chains and subsequently polymerizing the oligo-alkylene glycol functionalized isocyanopeptides.

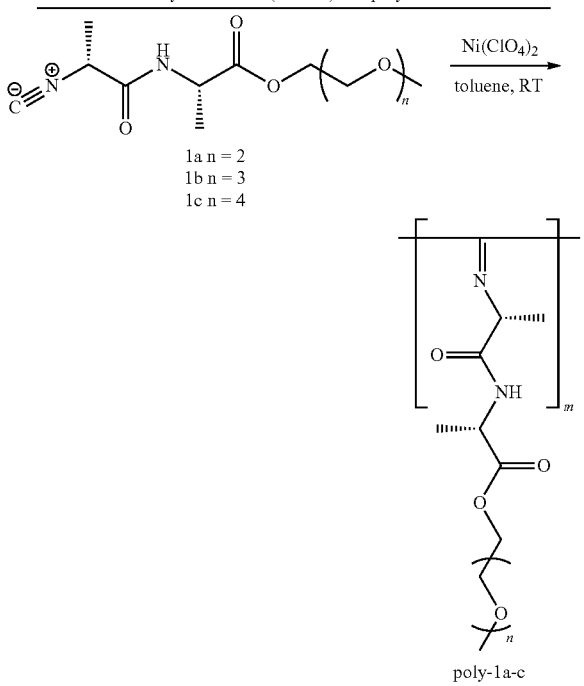

Scheme 1. Schematic representation of the polyisocyanide backbone isocyanides 1a-c (n = 1-6) and poly-1a-c.

Scheme 1 represents the synthesis described in WO 2011/007012. The "stiffness" of the resulting polymer is essential for its biomobility/bioefficiency properties. It required the polymerization of the above monomer, ethylene glycol peptidoisocyanides. This monomer may be modified to tailor the solubility and stiffness properties.

Scheme 2. Monomer used to make functionalized "nanosized wormlike polymers." Isocyanide monomers consisting of peptidic units (L or D, mono-, di-, tri- and tetra-peptides) connected to an oligoethylene tail, the connection can be via an ester or amide (shown above) of different length n = 1-8.

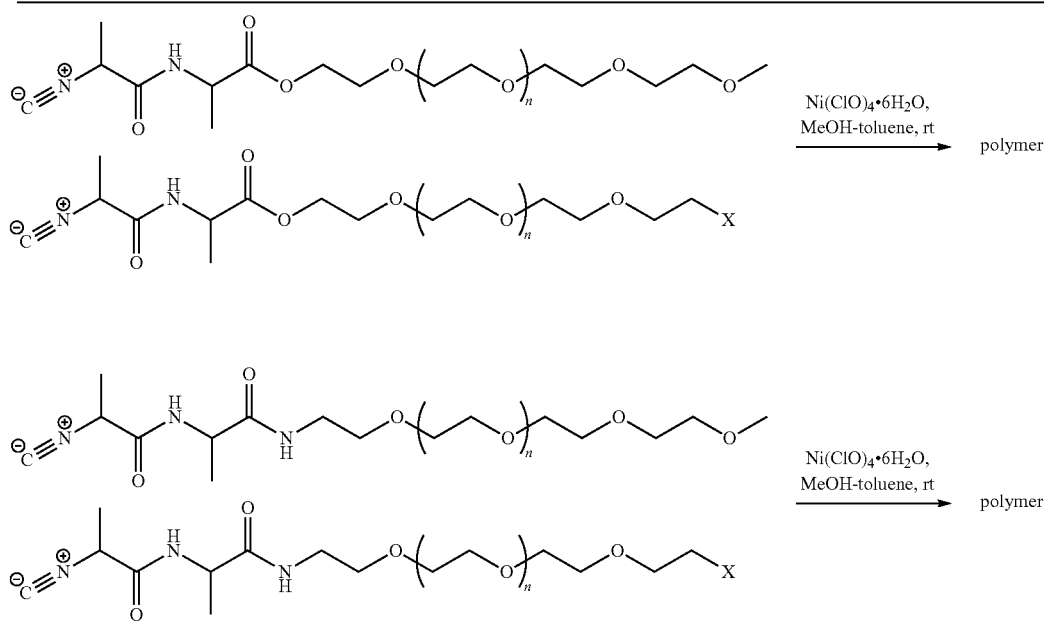

X = $N_3$, $NH_2$, acetylene, NHS, maleimide, vinyl sulfone, or any other functional group for conjugating biological molecules To make the functionalized nanosized wormlike polymers, the backbone is statistically modified every so many nanometers The functional polymer is a random copolymer, consisting of B and C (Scheme 3) mixed in differing ratios (1:10 to 10:1 ratio of B and C and all mixtures in between), giving a defined scaffold containing a functionalization position (X shown in scheme 2)

The terminal functional group attached to monomer C, which is a modified monomer of X, is shown as an azide in scheme 3), but this group can be any group that can be used for bioconjugation such as acetylene, maleimide, NHS-ester and other groups well known in the art.

To this functionalization unit, any biological molecule, drug molecule (drug delivery) and dye molecule (diagnostics) may be attached.

Scheme 3. Chemical structure of A) the "worm-like polymer" (R side chains defined by B and C), B) the predominant isocyanide monomer, C) azide functional monomer. Monomers B and C comprise from the left to the right: isocyanide partpeptide part; (water-compatible) polyethyleneglycol part. C contains an azide functional group at the end of the molecule. This may also be substituted with acetylene-containing extensions for click reaction, maleimide, NHS ester, or any other group that can be used for bioconjugation. D) TokyoGreen (fluorescein part).

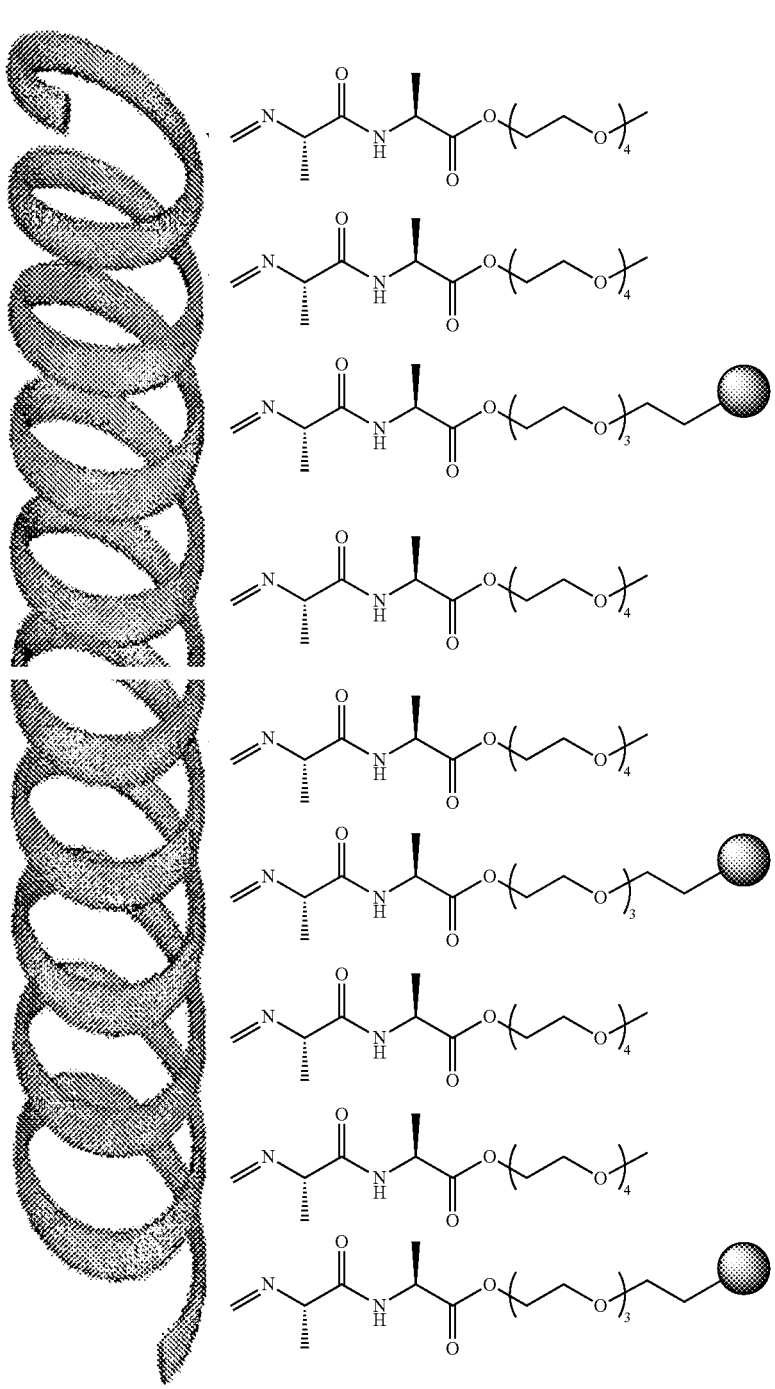

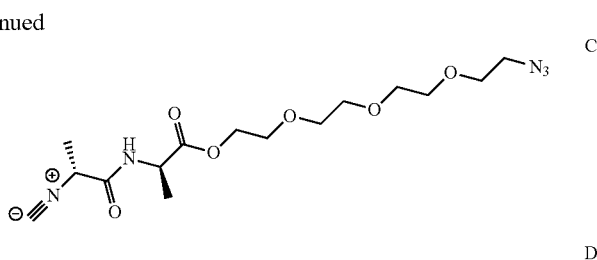

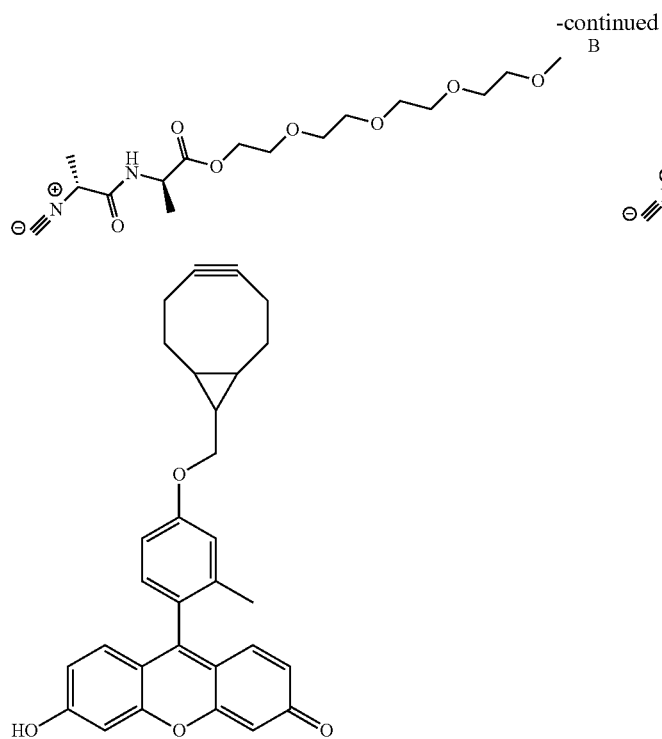

More in particular, in the present invention, a helical polymer may be used that is pharmaceutically acceptable, as may be determined by standard cell proliferation assays (for example, 3H-tritium incorporation, or by CFSE fluorescence measurements) using, for example, peripheral blood mononuclear cells (PBMCs), which can be considered as representative models. Thus, in one aspect, the invention uses as a carrier a filamentous polymer as described herein and, in particular, a helical polymer as described herein, that is pharmaceutically acceptable as determined by the in vitro cell proliferation assay used in Example 2. Similarly assays can be used to measure the cytotoxic activity of activated T-cells, such as cytokine release assays or assays that measure the amount of dead target cells (51 chromium release assays). Reference is, for example, made to Tel et al., *J. Immunol.* (2010) Apr. 15, 184(8):4276-83, Epub 2010 Mar. 19; Cruz et al., *J. Control Release* (2010) Jun. 1, 144(2):118-26, Epub 2010 Feb. 13; and Schaft et al., *J. Immunol.* (2003) Feb. 15, 170(4):2186-94.

With regard to helical polymers, it has been found that the helical structure generally provides the polymeric backbone with sufficient stiffness so that the polymeric fibers are prevented from rolling up or coiling up into a polymeric particle or "ball" (as would usually be the case for most polymeric fibers of the length set out herein). By means of illustration only and without limiting the invention in any way, it has been observed that water-soluble helical polymers of the type used in the invention are some of the stiffest water-soluble polymers known (and are, for example, more stiff than DNA).

The stiffness of the helical polymers used in the invention can, for example, be determined by means of suitable atomic force microscopy (AFM) techniques known in the art of polymer science.

The helical structure also provides the polymeric fibers with a degree of reptation ("snake-like" macromolecular motion, also sometimes referred to as "sereptation") and thus mobility, which is advantageous for a number of the applications and uses of the constructs of the invention envisaged herein (such as, for example, and without limitation, for in vivo immunological applications, where such mobility allows the constructs of the invention to migrate to a desired site of immunological action, such as a lymph node—further reference is made to the detailed description herein).

The mobility of the helical polymers used in the invention can, for example, be determined by determining rate of motion using suitable confocal microscopy techniques well known in the art of polymer science.

In addition, or alternatively, the constructs of the invention (or the helical polymers used therein) may be suitably labeled (for example, with a fluorescent label) and studied or observed using fluorescent microscopy. Also, electron microscopy techniques may be used.

The helical polymer that is used as a carrier in the constructs of the invention can be any suitable pharmaceutically acceptable helical polymer, but is preferably a helical polyisocyanide polymer (for which, generally, reference is again made to the prior art on helical polyisocyanides cited herein, such as, for example, the review by Nolte and the further references cited therein). Such helical polyisocyanide polymers can generally be prepared by techniques known per se, which generally involve helix-sensitive polymerization techniques (see again the prior art on helical polyisoyanides cited herein).

In the further description herein, the invention will mainly be described with reference to such helical polyisocyanide polymers, but it should be noted and it will be clear to the skilled person based on the disclosure herein that other suitable pharmaceutically acceptable filamentous or worm-like polymers (as described herein) and, in particular, other suitable pharmaceutically acceptable helical polymers, may also be used.

The helical polyisocyanide polymers used as a carrier in the constructs of the invention may be prepared starting from any suitable monomer or combination of monomers (or suitable oligomers). These will be clear to the skilled person based on the disclosure herein as well as the prior art on the preparation of helical polyisocyanide polymers cited herein and, as described therein, will usually be isocyanides. Any suitable isocyanide monomer or combination of isocyanide monomers can be used, and such isocyanide monomers can be prepared using suitable techniques of organic chemistry known per se. Some non-limiting examples of suitable isocyanide monomers can be found in the prior art cited herein.

One particularly preferred, but non-limiting class of isocyanide monomers that can be used to prepare the helical polyisocyanides used in the invention are isocyanide monomers that have been derived from amino acids and peptides. Techniques for converting amino acids into isocyanides that can then be used as monomers in the preparation of the helical polyisocyanides used in the invention are known in the art. Reference is again made to, for example, the review by Nolte and some of the further prior art on helical polyisocyanides cited herein.

When an isocyanide monomer is used that has been derived from an amino acid or a peptide, it can be derived from any suitable naturally occurring or non-naturally occurring amino acid or peptide, and may, for example, be an L-amino acid or a D-amino acid (or may have an R-confirmation or an S-confirmation, referring to the chiral center formed around the "alpha" carbon atom).

For example, in one specific, but non-limiting aspect, the helical polyisocyanide polymer used in the invention is a helical polyisocyanide that has been obtained by means of helix-sensitive polymerization of one or more isocyanide monomers that have been obtained from naturally occurring amino acids (such as, for example, and without limitation, using the standard three-letter amino acid code: Ala, Arg, Asn, Asp, Cys, Gln, Glu, Gly, His, Ile, Leu, Lys, Met, Phe, Pro, Ser, Thr, Trp, Tyr, Val; selenocysteine and pyrrolysine or any combination of two or more of such monomers derived from two or more different amino acids). However, it is well known that besides these 22 amino acids (which most occur in naturally occurring proteins and peptides), a large number of other amino acids have been found to occur in nature (such as, for example, hypusine, hydroxyproline, Gamma-carboxyglutamic acid/Gla) see, for example, the review by Musso, Angewandte Chemie International Edition in English, Vol. 22, 11, 816-828 (2003)), and these may also be used. Also, amino acids may be used that do not have the naturally occurring L-configuration at the alpha-carbon atom, but that instead have a D-configuration (such as D-alanine, D-arginine, etc.). Similarly, when a naturally occurring amino acid has an S-confirmation around the alpha-carbon atom, it is also possible to use the corresponding R enantiomer (or, in the case of cysteine, vice versa). It is further also possible to use amino acids in which the carboxyl-group is not bound to the same carbon atom as the amino group, and examples of such amino acids will also be clear to the skilled person. Thus, more generally, any isocyanide monomer that has been derived from any of these amino acids (or any suitable combination of two or more of such isocyanide monomers) may be used.

The helix-sensitive polymerization of these monomers may be performed in any suitable manner known per se, for which reference is again made to the prior art on helical polyisocyanides cited herein. Generally, this will involve the use of a suitable catalyst and other suitable polymerization conditions, as again described in the prior art.

The helical polymer obtained may be right-handed or left-handed; and as again described in the art on helical polyisocyanides, the handedness of the polymer obtained may be regulated by the choice of the monomer(s), the catalyst and/or the further reaction conditions. Reference is, for example, made to the review by Nolte, page 13 and the further prior art on helical polyisocyanides.

During polymerization, the length of the polymeric fibers obtained may be controlled in any suitable manner using techniques known per se in art of polymer chemistry, preferably so as to obtain fibers or filaments of the helical polymer with a length that falls within the ranges mentioned herein.

After polymerization, the fibers or filaments of the helical polymer may be recovered and purified/isolated using suitable techniques known per se, for which reference is again made to the prior art on helical polyisocyanides mentioned herein.

After polymerization, and prior to or after recovery/purification/isolation, the helical polymers may be made more water-soluble by attaching one or more groups or moieties that make the polymer more water-soluble (and/or by otherwise functionalizing or modifying the helical polymer (or functional groups present thereon) to make it more water-soluble). For example, and without limitation, the polymer may be made more water-soluble by attaching polyethylene glycol (PEG) groups or polymers such as, without limitation, PEG groups of between 1 and 50, such as about 4, 10 or 20 ethyleneglycol units. Alternatively, and/or in combination therewith, peptides or proteins (including, but not limited to, antibodies and antibody fragments) or other groups or moieties that function to increase the water-solubility of the constructs of the invention may be linked to the polymeric backbone, and it is envisaged that such peptides, proteins or other groups or moieties may also provide other desired and/or biological, immunological and/or other functional properties to the constructs of the invention. For example, and without limitation, some of the further "components" (as described herein) of the constructs of the invention may also be chosen so as to increase the solubility in water of the constructs of the invention.

It may also be possible to include, in the monomers or combination of monomers that are used as the starting materials for the polymerization reaction, one or more suitable monomers that already provide the helical polymer obtained with the desired solubility in water.

As generally described in the art of helical polyisocyanides, a suitable amount of the monomeric units present in the pharmaceutically acceptable helical polymers (and, in particular, most or essentially all of the monomeric units) will contain side chains (such as alanine side chains) that allow for the polymer to assume the helical conformation and/or that stabilize the helical confirmation in solution, for example, through Vanderwaals interactions or hydrogen bonds. This may, for example, be achieved by including a suitable amount of the corresponding monomer(s) in the polymerization reaction used to prepare the helical polymer.

The helical polymer used in the invention may or may not be biologically degradable (and, in particular, degradable in the human or animal body).

As already mentioned, for immunological and other pharmaceutical applications, one of the main advantages of the helical polymeric carrier used in the invention is that, because of its helical structure, the polymeric backbone has (and thus provides the constructs of the invention with) large flexibility and intrinsic mobility (both in vivo and in vitro), without rolling up into a polymer ball (which inherently would not provide the desired flexibility and mobility compared to the desired "worm-like" filaments used in the invention. This is a technical detail that should be well appreciated when considering the disclosure herein, namely that the great(er) degree of stiffness of the polymeric backbone of the polymers used in the invention means that the filaments cannot form a ball, which, in turn, means that the filaments retain a worm-like structure and, over all, retains more flexibility and mobility than a polymer with a more flexible backbone, which would roll up into a ball). After administration to a subject, this has advantages for the biodistribution, toxicity, migratory capacity and efficient cross-linking of receptors on the T-cell surface, as further described herein.

In addition to these advantages, which are of great value for in vivo immunological applications such as in immunotherapy, the use of the helical polymers in the constructs of the invention also provides a number of other advantages (in particular, compared to live APCs and/or compared to artificial APCs based on spherical or particulate carriers), such as any one or more of the following advantages, alone or in combination:

- Greater solubility, dispersibility or generally compatibility with aqueous media and physiological fluids;
- Ease of manufacture using suitable techniques of polymer chemistry (to prepare the helical polymer) and/or protein chemistry (to link the desired component(s) to the polymeric backbone);
- The constructs (for example, the components present therein) can be easily customized for individual patients.
- The manufacturing process for the preparation of the constructs of the invention may allow for greater control of the composition of the final constructs, as well as for improved quality control;
- Improved scalability of manufacture;
- Improved shelf-life;
- More conformational "degrees of freedom" for the components of the constructs, compared to proteins that are present on spherical or particulate carriers;
- The constructs may, because of their inherent mobility (as described herein) and because they are long, flexible and very thin (i.e., compared to APCs based on spherical carriers), in vivo provide an improved biodistribution to desired tissues or locations in the body of the subject to be treated (such as the lymph nodes), and/or other properties that make them more desirable for in vivo use.
- because of their snake-like or worm-like behavior under physiological conditions, they may be very well suited to cross-link multiple receptors (when antibodies against receptors are coupled) at a cell surface in general and as such induce intracellular signals.
- because of their filamentous nature, the constructs of the invention may better mimic mature DCs, which also contain large veils and filamentous extensions, which on the one hand facilitate DC migration, and on the other hand provide DCs with an enormous surface area to interact with multiple rare T-cells in the lymph nodes. The constructs of the invention may better mimic these properties of DCs than synthetic APCs based on spherical or other rigid carriers or backbones filamentous-shaped structures appear to persist significantly longer in the circulation than spherical-shaped structures upon injection in rodents, and might penetrate deeper into tissues and preferentially inside the T-cell area of a lymph node.

These and other advantages of the invention will be clear to the skilled person based on the disclosure herein.

DETAILED DESCRIPTION

Figure 1:
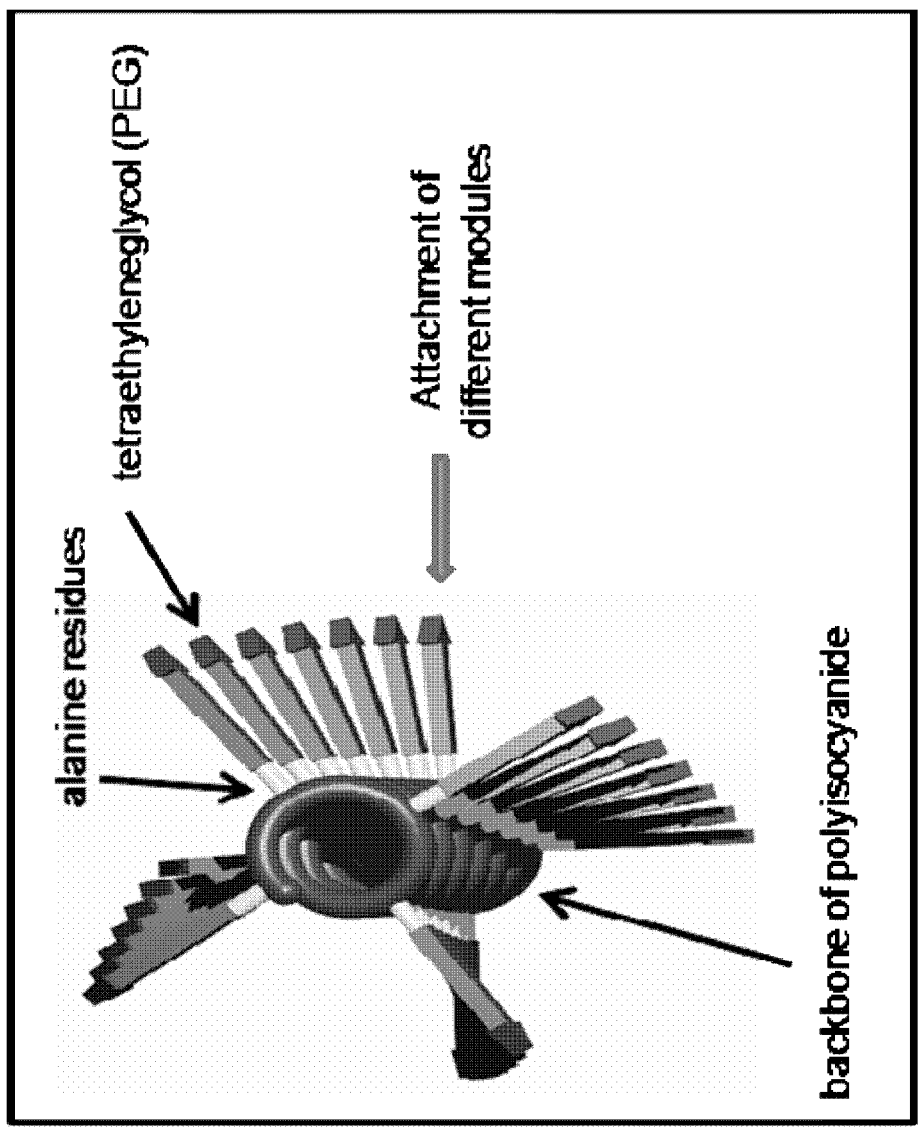
FIG. 1 is a schematic view of an example of a helical polymer backbone, functionalized with tetraethyleneglycol side-chains to increase water-solubility.

Thus, in one preferred, but non-limiting aspect, the invention provides a protein construct for presenting one or more antigens to one or more T-cells, which construct comprises at least one MHC complex and at least one further protein, peptide, factor and/or other component (as described herein), which are linked to (and are linked to each other via) a polymeric backbone that comprises a pharmaceutically acceptable helical polymer (as further described herein).

In a more specific (but also non-limiting) aspect, the invention provides a protein construct for presenting antigen(s) to one or more T-cells, which construct comprises at least one (and most preferably several, as further described herein) MHC complex and at least one (and preferably several, as further described herein) co-stimulatory factor(s) that is capable of activating or stimulating the T-cell(s) and/or that is capable of interacting with at least one (and preferably several, as further described herein) receptor on a T-cell, in which the MHC complex and at least one co-stimulatory factor are linked to (and are linked to each other via) a polymeric backbone that comprises a pharmaceutically acceptable helical polymer (as further described herein).

Preferably, the constructs of the invention contain multiple copies of one or more MHC complexes (which, when there are more, may be the same or different, as further described herein) and multiple copies of one or more co-stimulatory molecules (which, when there are more, may be the same or different, as further described herein). It is also envisaged that constructs of the invention that comprise multiple copies of one or more MHC complexes and/or one or more co-stimulatory molecules may in vivo provide for T-cell cross-linking and as such may further increase the desired T-cell activation.

In another aspect, the invention provides a protein construct for T-cell induction, activation or suppression, which contains at least one (first) component that can provide an antigen-specific signal to a T-cell and at least one (second) component that can provide an antigen non-specific signal to said T-cell, which are linked to (and are linked to each other via) a polymeric backbone that comprises a pharmaceutically acceptable helical polymer (as further described herein).

The constructs according to the above aspects of the invention, which are also referred to herein as "antigen-presenting constructs," may be as further described herein. For example, as further described herein, these antigen-presenting constructs may also comprise the one or more antigen(s) to be presented to the one or more T-cells (and/or any suitable antigenic part(s), fragment(s), epitope(s) or antigenic determinant(s) thereof, for example, as part of an MHC/antigen complex with the at least one MHC that is present in the constructs of the invention, and/or in any other form that allows the construct to suitably present the antigen(s) to the one or more T-cells (preferably so as to activate the T-cells and/or to raise an immune response against the one or more antigens. Antigens and antigenic peptides that can be presented using the constructs of the invention will be clear to the skilled person based on the disclosure herein (see, for example, the further description herein).

However, although the invention will now be described in more detail with particular reference to constructs that are directed toward T-cells, it should be noted (and will be clear to the skilled person based on the disclosure herein) that the polymeric carriers described herein can also be used to provide constructs that are directed toward other cells of the immune system, such as (without limitation) NK-cells or NKT-cells or B-cells, or macrophages, or stem cells or progenitor cells. Thus, the constructs of the invention may also be tailored (by suitable choice of the components present therein) toward interaction and/or modulation with other cells involved in the immune system or immune response (such as, again, NK-cells or NKT-cells or B-cells, or macrophages, or stem cells or progenitor cells) and such constructs of the invention and their applications and uses form further aspects of the invention.

Thus, in a more general aspect, the invention also relates to a protein construct for presenting one or more antigens to one or more T-cells, which construct comprises at least one complex or molecule capable of presenting an antigen to a T-cell and at least one further protein, peptide, factor and/or other component (as described herein), which are linked to (and are linked to each other via) a polymeric backbone that comprises a pharmaceutically acceptable helical polymer (as further described herein). As mentioned herein, the complex or molecule may be in the form of a complex with (or otherwise associated with) the one or more antigens to be presented. In a specific aspect, the complexes or molecules may be chosen from MHC complexes and/or CD1d molecules (or any suitable combination of two or more MHC complexes and/or CD1d molecules). Constructs containing MHCs may, in particular, be used to present (peptide) antigens to T-cells that recognize MHC complexes, whereas constructs containing CD1d molecules may be used to present (lipid) antigens to T-cells that recognize CD1d-presented antigens (such as NKT-cells). It is also envisaged within the scope of the invention that the constructs of the invention contain both one or more MHC-complexes and/or MHC-antigen complexes and one or more CD1d molecules and/or CD1d/antigen complexes (and further components as described herein), and it is envisaged that such molecules could be used to stimulate both T-cells recognizing MHC and NKT-cells.

In a more specific (but also non-limiting) aspect, the invention provides a protein.

The one or more co-stimulatory factors that are present in the antigen-presenting constructs of the invention may, for example, be chosen from co-stimulatory factors that can interact with one or more receptors on the intended T-cell(s), that can induce or activate the intended T-cell(s), and/or that can enhance or increase (or alternatively, suppress or decrease) one or more immunological activities of the T-cell(s). Suitable examples of such co-stimulatory factors will be clear to the skilled person based on the disclosure herein. For example, when the constructs of the invention are to be used as "artificial" or "synthetic" analogs of naturally occurring APCs (and, in particular, as "artificial" or "synthetic" DCs), the co-stimulatory factors may, for example, be any suitable co-stimulatory factors that are expressed by and/or present on the surface of the corresponding "native" APC (and, in particular, on the surface of DCs). However, other suitable co-stimulatory factors for T-cells may also be used (such as those used in the art for making artificial APCs), and it will also be clear to the skilled person that the invention allows for different (types of) co-stimulatory factors (such as, for example, co-stimulatory factors that have been derived from, and/or that are naturally present on, different kinds of APCs) to be combined in a single construct. In this manner, a combination of optimal stimulation signals can be incorporated in the constructs of the invention to achieve selective stimulation of specific T-cell populations.

Some preferred, but non-limiting examples of co-stimulatory factors that may be present in the constructs of the invention are: B7.1/CD80, B7.2/CD86, CD2, CD27, 4-1BB and/or CD40, or any suitable combination thereof.

Instead of (and/or next to) a co-stimulatory factor, the constructs of the invention may also contain one or more other proteins, ligands or binding domains that are capable of binding to and/or interacting with the receptor for a co-stimulatory factor on a T-cell, so as to provide the same or similar immunomodulatory effect to the native co-stimulatory factor(s). Examples can be binding domains that can bind to the same receptor(s) on the T-cell as the relevant co-stimulatory factor(s), which binding domains may, for example, be antibodies, antibody fragments (such as VH, VL, Fab fragments or ScFvs) or other immunoglobulin binding domains. These may, for example, be directed against receptors on T-cells such as CD28, 4-1BB, OX-40 or LFA-1. Also, as mentioned, cytokines, chemokines and/or other (soluble) factors may be included in the constructs of the invention.

Also, as generally described herein for any component of the constructs of the invention, where the constructs of the invention contain a co-stimulatory factor, it may contain a single copy of such a co-stimulatory factor (if this is sufficient to attain the desired immunomodulatory effect) or it may contain multiple copies thereof, and this may also increase or enhance the intended immunomodulatory effect, for example, through avidity effects (which may increase binding to the T-cells) and/or by providing the construct with the ability to interact with and/or to activate multiple receptors on the T-cell at the same time, and/or to cross-link different receptors on the T-cell. It will be clear that for this purpose, it is of advantage that the constructs of the invention allow for different co-stimulatory factors to be included in a single construct, with improved control over the composition of the construct, and also with increased flexibility and improved "degrees of freedom" (entropy) for the special confirmation of the different components present in the construct (i.e., compared to artificial APCs that comprise a spherical or particular carrier). It is also possible that, where a construct of the invention contains a co-stimulatory factor, it contains two or more different variants, analogs, etc., of the co-stimulatory factor, for example, so as to have an increased range of specificities for different (cognate) receptors on T-cells (or even for different T-cells) built into the construct.

In addition to the at least one suitable MHC complex and the at least one suitable co-stimulatory factor, the antigen-presenting constructs of the invention may also comprise one or more further suitable components (as further described herein), which may also be (and preferably are) linked to the polymeric backbone (and are preferably linked to each other via the polymeric backbone). These one or more further components present in the antigen-presenting constructs of the invention may, for example, be chosen to confer any suitable or desired immunomodulatory effect(s) to the constructs of the invention (in particular, but not exclusively, on T-cells), may enhance the binding of the construct to T-cells, may enhance the desired properties or effects of any other components present in the construct (which may also lead to a synergistic effect) and/or may confer one or more other desired and/or advantageous pharmaceutical and/or immunological properties to the constructs of the invention. Suitable components will be clear to the skilled person based on the disclosure herein and, for example, include those components that have been used in the art in the preparation of artificial APCs (for which, generally, reference is, for example, made to Steenblock et al. (2009), Chang, Lu et al., Oelke et al., Zhang et al., Greensmith and Aickelin, Steenblock et al. (2008), Chang et al. (2006), Maus et al., Rudolf et al., Goldberg et al., and Caserta et al., all cited above in the paragraph describing APCs known in the art, as well as to, for example, U.S. Pat. No. 6,787,154), those components that have been used in the art in constructs that comprise one or more MHC complexes, as well as the further components for the constructs of the invention mentioned herein.

For example, WO 97/46256 describes MHC-class II antigen-presenting systems that comprise a synthetic antigen-presenting cell that expresses a recombinant MHC class II molecule in combination with one or more "accessory molecules" (which include co-stimulatory molecules, survival molecules and adhesion molecules), and it is envisaged that the antigen-presenting constructs of the invention form an advantageous alternative to the cell-based APCs described in WO 97/46256 and may contain, next to the one or more MHC complexes, one or more of these "accessory molecules" as described in WO 97/46256. Reference is particularly made to the description of such accessory molecules on pages 21 to 24 of WO 97/46256. It is also envisaged that, as described in WO 97/46256 for the cell-based APCs described therein, that the presence of one or more of such accessory molecules may allow the constructs to be tailored depending on the desired outcome for effecting proliferation and phenotypic activation of the intended T-cells (such as $CD4^+$T-cells). In such a case, it is envisaged that the constructs of the invention may be used for the same purposes, uses and applications as described in WO 97/46256 for the cell-based APCs described therein.

Thus, for example, the constructs of the invention can generally contain one or more (and preferably two or more) of the following components:

- one or more MHC complexes or MHC-antigen complexes (as already described herein for the antigen-presenting constructs of the invention);
- one or more CD1d molecules, or complexes of a CD1d molecule and an antigen (in particular, a lipid or glycolipid antigen);
- one or more co-stimulatory factors, such as B7.1/CD80, B7.2/CD86, CD2, CD27, 4-1BB and/or CD40;
- one or more other proteins, peptides, ligands, etc., that are expressed by/expressed on the surface of APCs (such as DCs), for example, those that are involved in APC/T-cell interaction/adhesion and/or in the activation of T-cells by APCs, such as ICAM-1, ICAM-2, ICAM-3, LFA-1, CD2, CD62 and/or LFA-3 (CD58);
- one or more (other) proteins, peptides, ligands, factors or other compounds that are involved in APC/T-cell interaction and/or in the activation of T-cells by APCs, such as CTLA-4;
- one or more (other) ligands of receptors on T-cells or other compounds that have an immunomodulatory effect (for example, on a T-cell or generally on the immune system of a subject to be treated). Examples are ligands interacting with CD40L, CTLA-4, CD4, CD8, CD2, 4BB1L, or TCR, BCR, NKTCR;
- one or more other components that can be included in artificial APCs (for which reference is, for example, made to the prior art cited herein), such as the "survival molecules" mentioned in WO 97/46256, including, without limitation, Fas ligand, TNF receptor, TNF or CD70;
- antibodies, antibody fragments (such as VH, VL, ScFv and Fab fragments) and other binding domains or binding units that can bind to (receptors on) T-cells and/or that can activate or modulate T-cells. One example thereof are antibodies or antibody fragments that are directed against CD28, CTLA-4, CD40L, CD2, 4BB1L, CD4 or CD8;
- one or more components that allow the constructs of the invention to be targeted to specific T-cells, to specific parts or tissues of the body, of the circulation or of the lymphatic system, for example, an antibody or antibody fragment against an endothelial adhesion molecule selectively expressed in the lymph nodes (for example, VAP-1 or PNAd);

suitable markers, such as radiolabels, (chemo)luminescent or fluorescent markers, markers for nuclear magnetic resonance, etc. As mentioned, these may, for example, be used to observe the constructs of the invention (in vitro or from samples taken in vivo) using fluorescent microscopy techniques;

cytokines such as, for example, IL-2 or IL-12 and/or chemokines such as, for example, CCL-19 or CCL-21;

therapeutic payloads (for example, cytotoxic groups) and therapeutic entities or compounds, such as therapeutic antibodies and antibody fragments, protein, peptide, or other biological drugs or small molecule drugs;

one or more sugars, glycolipids, lipids;

or any suitable combination of the foregoing.

In a more general aspect, the invention relates to constructs that can be used for therapeutic or prophylactic purposes and that contain a pharmaceutically acceptable helical polymeric backbone as described herein. In these constructs, generally, two or more proteins, peptides, factors, subunits, binding units or other compounds or biological moieties (which may be the same or different, and at least one of which will be able to provide a desired biological and/or therapeutic effect) will be linked to (and linked to each other via) the helical polymeric backbone. The invention also relates to the use of a pharmaceutically acceptable helical polymeric backbone (as described herein) in (the preparation of) such therapeutic or prophylactic constructs.

Also, generally, when the constructs of the invention contain any protein, peptide, factor, subunit, binding unit or other compound or biological moiety, it may contain a single copy of such a component (if this is sufficient to attain the desired biological and/or therapeutic effect, such as an immunomodulatory effect), or it may contain multiple copies thereof, which may also increase or enhance the intended biological and/or therapeutic effect, for example, through increased binding (for example, to a T-cell or other suitable cell of the immune system), through avidity effects, and/or by having the ability to interact with and/or to activate multiple receptors (for example, on a T-cell) at the same time. It is also possible that, where a construct of the invention contains a protein, peptide, factor, subunit or other compound, it contains two or more variants, analogs, etc., of the component, for example, so as to have an increased range of specificities built into the molecule, for example, for different (cognate) target receptors or even for different cells or tissues.

Generally, when the constructs of the invention are intended to be used for immunotherapy or other immunological purposes, they will generally contain (and/or may be designed to contain) one or more suitable components (as described herein) that confer on the constructs the ability to achieve (either in vitro, ex vivo and/or, upon suitable administration to a subject to be treated, in vivo) a desired or intended immunomodulatory response or effect. As such, constructs of the invention containing one or more such components may generally be designed and used to induce, enhance or suppress a desired immune response in a cell and/or in a subject to be treated.

In particular, in one non-limiting aspect, the protein constructs of the invention can contain (and/or may be designed to contain) one or more components (as described herein) that allow the protein constructs of the invention to interact with at least one T-cell (again, either in vitro, ex vivo and/or in vivo), so as to modulate the activities of the at least one T-cell in a desired or intended manner.

For this purpose, the protein constructs of the invention will generally contain one or more such components (as described herein) that can interact with one or more T-cells, that can activate or induce one or more T-cells, that can enhance or increase (or, alternatively, suppress) one or more immunological activities of a T-cell, and/or that can bind to a T-cell (and, in particular, to one or more receptors or other cell surface-expressed proteins on the T-cell(s)). Suitable examples thereof will be clear to the skilled person based on the disclosure herein, and include, but are not limited to, MHC complexes, co-stimulatory factors and some of the further components mentioned herein.

For example, as already mentioned herein, the constructs of the invention may contain (and may be designed to contain) such components so as to allow the constructs to present a desired antigen to a T-cell and/or to raise or enhance (or alternatively suppress) an immune response against a desired antigen. In such a case, as further described herein, the constructs of the invention may contain such an antigen (or one or more suitable antigenic parts, fragments, epitopes or antigenic determinants thereof) such that the constructs have the ability to present the antigen to a T-cell and/or to raise an immune response against the antigen, optionally in the form of an antigen-protein complex with a protein that is capable of suitably presenting the antigen (or one or more suitable antigenic parts, fragments, epitopes or antigenic determinants thereof) to such a T-cell, and/or to raise an immune response against such an antigen.

In particular, according to one preferred, but non-limiting aspect that has already been referred to above, such antigen-presenting constructs of the invention may contain at least one MHC complex (in a single copy or, most preferably, in multiple copies). The MHC complex may be any suitable MHC complex, but is preferably an MHC complex (or any suitable part(s), fragments(s) or subunit(s) thereof, optionally in a suitable combination) that, when present in the constructs of the invention, has/retains the ability to interact with the intended T-cell(s) (for example, in the subject to be treated and/or, alternatively, ex vivo), and, in particular, has/retains the ability to modulate the intended T-cell(s) (most preferably, so as to raise the intended immune response in the subject to be treated), to present an antigen to the intended T-cells (most preferably, so as to raise an immune response against the antigen), and/or to interact with the intended (cognate) T-cell receptor(s) on the T-cell.

Also, as generally described herein for any components that may be present in the constructs of the invention, the constructs of the invention may contain two or more copies of an MHC and/or may contain two or more different types, kinds, variants or analogs of an MHC, and it is generally within the scope of the invention that the presence of such multiple copies and/or different variants may (further) enhance or increase the desired immune response by the T-cell and/or in the subject to be treated (or, where desired or appropriate, further suppress an unwanted or excessive immune response). For example, different types of MHC molecules can be used to cover one or more (or essentially all) HLA types (which may avoid the limitation to HLA-A2, which is common when working with live DCs.

For example, the international applications WO 09/003,492 and WO 08/116,468 describe MHC multimers and their use in the field of immunology and immunotherapy. It is envisaged that the polymeric backbone of the invention may also find use in providing and/or stabilizing such MHC multimers, for example, by coupling multiple copies of the same (or different) MHCs onto the same polymeric backbone, using the methods and techniques described herein. Because of the flexibility of the polymeric backbone, it may also be possible to incorporate different parts, fragments and/or subunits of (different) MHC complexes into a construct of the invention, which may then combine in the correct spacial conformation to form a functional MHC complex (including complexes that may not normally be found in the subject to be treated).

Similarly, the international application WO 08/116,468 describes MHC-peptide complexes and MHC multimers, in which the MHC monomers are suitably linked to each other via one or more "multimerization domains" to form a MHC multimer. As examples of suitable multimerization domains, cells, solid supports and "molecules" (including a range of difference polymers) are mentioned.

It is also envisaged in the invention that constructs of the invention that contain only MHC complexes (but no co-stimulatory factors and preferably no other components that can induce or activate T-cells) can be used to induce anergy of T-cells, and such constructs and their use form a further aspect of the invention.

Thus, in one aspect of the invention, the constructs of the invention contain or comprise the polymeric backbone described herein, to which are bound at least two or more copies of an MHC (which may be the same of different), and optionally one or more further suitable components of the constructs of the invention as described herein.

The MHC complex(es) present in the constructs of the invention may be an MHC-I or MHC-II complex, or any desired or suitable combination thereof. With respect to constructs of the invention that comprise a combination of one or more MHC class I complexes (preferably, as already stated herein, in multiple copies) and of one or more MHC class II complexes (again, preferably, as already stated herein, in multiple copies), it is envisaged that, according to the invention, such constructs may both activate CD4 cells (and thus provide for the cytokine production/release mediated by CD4$^+$ T-cells) and at the same time activate CD8$^+$ cells (both via the MHC class I complex present in the construct as well as via cytokines that are released by the interaction of the MHC class II complexes in the constructs and the CD4+ T-cells). It is also envisaged that such constructs may "cross-link" CD4$^+$ and CD8$^+$ T-cells and/or bring/keep such cells in close proximity to each other, which may again provide for an improved/increased immune response.

For some examples of suitable MHC complexes (or suitable parts, fragments or subunits thereof) that may be present in the constructs of the invention, reference is, for example, made to Rodenko et al., *Nat. Protoc.* (2006) 1(3):1120-32; Bakker et al., *Proc. Natl. Acad. Sci. U.S.A.* (2008) 105(10):3825-30; and Toebes et al. *Curr. Protoc. Immunol.* (2009) Chapter 18, Unit 18.16 and the further references cited therein. Also, it will be clear to the skilled person that the constructs of the invention may also contain any suitable MHC complex that has been used in the art in the preparation of artificial APCs. These may be naturally occurring MHC complexes or synthetic/recombinant MHC complexes. As a non-limiting example thereof, reference is, for example, made to the recombinant MHC complexes that are present in the APCs described in WO 97/46256 already referred to herein.

Where the constructs of the invention contain one or more antigens (for example, for presentation to T-cells), these are usually and preferably present as a suitable complex with the one or more of the MHCs present in the constructs of the invention (although the invention in its broadest sense is not limited thereto), such that the constructs of the invention (and, in particular, the MHCs present therein) can suitably present the antigen(s) to the immune system of the subject to be treated (and, in particular, to at least one T-cell in the subject to be treated, either in vivo or ex vivo).

To obtain suitable MHC-antigen complexes, it is, for example, also possible to ex vivo pulse or transform APCs that express a suitable MHC with the desired antigen(s), and then suitably isolate the MHCs from these APCs once they have started to express or display the desired antigen(s) (or suitable antigenic parts or fragments thereof). These MHCs may then be used in the constructs of the invention. Other techniques for providing suitable MHC-antigen complexes for use in the constructs of the invention will be clear to the skilled person based on the disclosure herein and, for example, include those mentioned in Rodenko et al., Bakker et al., and Toebes et al. (all supra), and the further references cited therein, as well as the methods and techniques that have been used in the art for making MHC-antigen complexes for use in artificial APCs (which may also include the use of cells that contain or express one or more suitable "antigen processing assisting molecules," such as HLA-DM and invariant chain). Reference is, for example, again made to WO 97/46256.

Thus, in one aspect of the invention, the constructs of the invention contain or comprise the polymeric backbone described herein, at least one MHC-antigen complex, and one or more further suitable components of the constructs of the invention as described herein. Again, these constructions, preferably, also contain at least one co-stimulatory factor as described herein.

Also, as mentioned herein, the constructs of the invention may be designed to present antigens (and, in particular, lipid antigens) to NKT-cells. In such a case, the constructs of the invention do not necessarily need to contain an MHC, but will contain one or more CD1d molecules (preferably in complex with or otherwise associated with the lipid antigen or antigens); and most preferably, also one or more stimulatory factors for NKT-cells (and/or one or more other proteins, peptides, ligands, etc., that are involved in APC/NKT-cell interaction and/or in the activation of NKT-cells by APCs), as well as, optionally, one or more further components of the constructs of the invention as mentioned herein.

When the constructs of the invention are designed to present one or more antigens to the immune system of a subject to be treated (and, in particular, to one or more T-cells of the subject to be treated), the antigen may be any antigen against which an (enhanced) immune response is to be induced in the subject. For example, in one preferred aspect, the antigen may be a suitable tumor antigen (for example, a tumor antigen expressed by a tumor present in the subject to be treated), in which case, the protein constructs of the invention may be used in cancer immunotherapy in the subject to be treated. Suitable tumor antigens and/or methods for obtaining them (for example, from a tumor present in a subject to be treated) will be clear to the skilled person based on the disclosure herein.

For example, the constructs of the invention may contain, and may then be used to present, one or more "tumor-associated antigens" or "TAAs," for which reference is, for example, made to the review by Tuyaerts et al., "*Current approaches in dendritic cell generation and future implications for cancer immunotherapy,*" *Cancer Immunol. Immunother.* (2007), vol 56, 1513-1537; to Van Der Bruggen et al., *Immunological Reviews* (2002), vol. 188, 51-64; and to the review by Novellino et al., *Cancer Immunol. Immunother.* (2005) 54:187-207, which provide a list of human tumor antigens that can be recognized by T-cells, which can also be presented using the antigen-presenting constructs described herein. Other suitable tumor antigens are, for example, disclosed in WO 05/061537. Also, other suitable antigenic proteins or peptides may be used, such as the multiepitope polypeptides based on TAAs as described in WO 05/028505.

Alternatively, and/or in addition, the constructs of the invention may contain one or more antigenic peptides, such as anti-tumor peptides, for example, those described in Bakker et al., *J. Exp. Med.* (1994) Mar. 1, 179(3):1005-9; and Bakker et al., *Int. J. Cancer* (1997) Jan. 27, 70(3):302-9.

Other suitable types of antigens or antigenic peptides that may be present in and/or presented using the constructs of the invention will be clear to the skilled person and will generally comprise any type of antigen that can be presented to the immune system of a subject to be treated (and, in particular, to at least one T-cell in the subject to be treated) so as to obtain the desired immune response. Some non-limiting examples of such antigens or antigenic peptides are those mentioned in the prior art cited in the preceding paragraphs as well as in, for example, Schaft et al., *J. Immunol.* (2003) Feb. 15, 170(4):2186-94; and de Vries et al., *J. Clin. Oncol.* (2005) Aug. 20, 23(24):5779-87.

When the compounds of the invention contain an antigen or an antigen-protein complex (such as an antigen-MHC complex), it may again contain a single copy or multiple copies of the antigen or complex, and it is within the scope of the invention that the presence of multiple antigen(s) or complexes in the constructs of the invention will provide an enhanced immune response against the antigen(s) in the subject to be treated. Also, the constructs of the invention may be designed so as to contain two or more different antigens and/or two or more analogs or variants of the same antigen (again, also as antigen-protein complexes). For example, the constructs of the invention may contain two or more antigens that are expressed by the tumor to be treated in the subject. Again, as generally described herein, the greater control provided by the invention (compared to the use of live cells or spherical or particulate synthetic DCs) over the composition of the constructs of the invention, i.e., the component(s) present therein, their amount(s) and their ratio(s), may allow the artisan to better control and/or tailor the antigen(s) present in the constructs (as well as their amount(s) and their ratio(s)). This may allow the artisan to better control the intended or desired immune response(s) that is/are obtained through the use of the constructs of the invention.

As already mentioned herein, where the constructs of the invention contain one or more antigens, these antigens are preferably present in a form that allows them to be suitably presented to the immune system of a subject to be treated (and, in particular, to at least one T-cell in the subject to be treated). For this purpose, the antigen(s) are preferably present as part of a suitable MHC-antigen complex, as already described herein. However, it is not excluded that the constructs of the invention contain one or more copies of the antigen(s) that are not part of such a MHC-antigen complex, but that, for example, are directly linked to the polymeric backbone or bound/linked to or otherwise associated with another component of the constructs of the invention. The presence of such a "naked" antigen may provide additional immunomodulatory and/or biological effects.

The international application WO 06/083874 describes vaccine delivery compositions for immunotherapy based on polyester amide, polyester urethane or polyester urea polymers. It is stated that these vaccine compositions may comprise one or more suitable antigens, and it is also suggested that these antigens may be linked to the polymeric carrier. However, apart from the differences in the polymers used, it should be noted that the vaccine compositions described in WO 06/083874 are used to present the antigen (s) to APCs, which then take up the vaccine compositions and present the antigens to T-cells. Thus, WO 06/083874 is not directed to providing artificial APCs.

As will be clear from the disclosure herein, one of the main envisaged uses of the constructs of the invention is to serve as "artificial" or "synthetic" APCs that can be used to present the antigen(s) to a T-cell (either in vitro, ex vivo or in vivo) and, more generally, the immune system of a subject to be treated (and, in particular, to at least one T-cell in the subject to be treated), so as to induce or enhance an immune response in the subject against the antigen(s). As mentioned, depending on the antigen(s) used, this aspect of the invention can find use in immunotherapy of tumors, of infectious diseases and other diseases or disorders that are amenable to prophylaxis and/or treatment using immunotherapy.

However, it should be noted that alternatively, constructs of the invention that can present one or more antigens may also be used, where desired or appropriate, to (specifically and usually temporarily) suppress immune responses and/or to induce or increase tolerance against the antigens. It is envisaged that constructs of the invention that have been designed for this purpose may, for example, be used in treating allergy or autoimmune disorders caused by an undesired, deleterious and/or excessive immune response in the subject to be treated (for example, autoimmune diseases such as rheumatoid arthritis), but also, for example, to prevent rejection after organ transplantation. Based on the disclosure herein, the skilled person will be able to suitably design and prepare such a "tolerogenic" construct of the invention (i.e., by suitably choosing the antigen(s) and other components present therein) and to use the same to obtain a desired "tolerogenic" immune response in a subject to be treated.

It should also be noted that the constructs of the invention may be used to present an antigen to, to modulate and/or to exert another desired immunomodulatory effect on any suitable or desired T-cell, including, but not limited to, CD4+ T-cells, $CD8^+$ cytotoxic T-cells, Th1 cells/inflammatory T-cells, Th2 cells/T helper cells, Th17 cells and/or Treg cells. As mentioned herein, it is envisaged that the constructs of the invention, by suitable selection of the components present therein, may be tailored toward a specific subset of T-cells and/or toward a desired outcome for effecting proliferation and phenotypic activation of the intended T-cells or subset of T-cells. For example, it is known that usually, antigens presented by Class I MHC molecules will be (preferentially) recognized by $CD8^+$ cytotoxic T-cells, whereas antigens presented by Class II MHC molecules are usually (preferentially) recognized by CD4+ T-cells. It is, for example, also envisaged that the constructs of the invention may be designed or tailored so as to induce (certain subsets of) T-cells to differentiate in a certain direction (for example, to direct $CD4^+$ cells to differentiate in the direction of Th1, Th2 or Th17 cells) and/or to induce T-cells (and, in particular, $CD4^+$ cells) to produce specific cytokine(s).

When the constructs of the invention are intended for use in a human subject (for example, for immunotherapy), the components present in the constructs are preferably derived from a human (i.e., preferably essentially have an amino acid sequence that naturally occurs in man). However, where the constructs of the invention are intended for use with another species of animal/mammal (for example, when the constructs of the invention are intended for use in a suitable animal model), the components present in the constructs may also be derived from the animal/mammal.

The proteins, peptides, factors or other components can be linked to the polymeric backbone in any suitable manner, usually via covalent linkage. For this purpose, either the polymer and/or the one or more proteins, peptides, factors or other components to be linked to the polymer, can, for example, be chemically activated and/or provided with suitable residues or moieties that allow for covalent attachment of the proteins, peptides, factors or components to the polymeric backbone. Examples of suitable chemistries for linking proteins and peptides to organic polymers will be clear to the skilled person and, for example, include linking chemistries based on EDC (1-Ethyl-3-[3-dimethylamino-propyl]carbodiimidehydrochloride), dimethyladipimidate (DMA), dimethyl suberimidate (DMS) and dimethyl pimelimidate (DMP) with spacer arms of 8.6 Å, 11 Å and 9.2 Å, respectively, and other standard chemistries and functional groups for linking proteins and peptides to organic molecules or polymers. Alternatively, the components can be linked to one-half of a suitable binding pair (for example, biotin or streptavidin) and the polymeric backbone can be provided with the other half of the binding pair, whereupon the components can be linked to the backbone via formation of the binding pair (see Example 1 of a non-limiting example of the use of such a binding pair).

In the invention, the proteins, peptides, factors or other components may be linked to the polymeric backbone (optionally, via a suitable linker or spacer), provided this does affect too much the desired flexibility, motility and other desired properties of the backbone and/or the final constructs. Usually, however, the proteins, peptides, factors or other components will be linked to one of the side chains of the backbone, again, optionally, via a suitable linker or spacer. For example, where the side-chains are provided with PEG groups to increase the water-solubility of the constructs, the proteins, peptides, factors or other components may be linked to the PEG groups, which then both serve to increase water solubility and also as a linker or spacer to attach the proteins, peptides, factors or other components to the (side chains of) polymeric backbone. This is also schematically shown in the non-limiting and illustrative FIG. 1, which schematically shows a polymeric backbone of the invention that has been functionalized with PEG groups on the side chains to increase water solubility, with attachment of the proteins, peptides, factors or other components foreseen at the end of the PEG groups.

Again, where the proteins, peptides, factors or other components are linked to the side chains and/or via a spacer or linker, the proteins, peptides, factors or other components may be covalently linked to the side chain, spacer or linker or via the formation of a suitable binding pair. Generally, for all the applications of the constructs of the invention as described herein, it will be clear to the skilled person that, compared to the use of live DCs or even spherical or particulate "synthetic" DCs, that the fact that the constructs of the invention can be prepared using specific chemical protein coupling techniques and reactions that are well established in the field of protein chemistry, as well as the fact that the conditions for such coupling reactions can generally be (more) tightly controlled compared to working with live cells (for example, by using different protective groups and/or separate reactions steps or reaction conditions), allows the artisan to exert and retain a much greater degree of control over the composition of the final constructs (i.e., type and number of the proteins, peptides, factors, subunits or other compounds present therein, as well as their stochiometry). This is another advantage of the constructs of the invention. Also, compared to live cells (which need to be kept viable) or even spherical or particulate "synthetic" DCs, the use of the polymeric backbone in the constructs of the invention may make it possible or easier to (better) characterize the constructs after they have been made (for example, for purposes of quality control). It is also envisaged that, because the polymer used in the constructs of the invention may be prepared using well-known techniques in the field of polymer chemistry for controlling the (average) composition of the polymer and/or the amounts, order and/or stochiometry of the different building blocks present therein, the helical polymer used in the invention may be prepared so as to carry well-defined activated sites or functional groups for protein attachment (for example, with a well-defined distance or average distance between the attachment sites on the polymer, and/or with a well-defined (average) number of functional/activated groups and/or ratio of different groups on the polymer). For example, different chemistries, different activated/functional groups and/or separate reaction steps may be used to attach different components of the constructs of the invention. This may also allow greater control over the final composition of the constructs of the invention, and may even allow the constructs to be designed to have a desired or optimal (average) distance or spacing between the various components present in the constructs (for example, so as to improve binding or avidity and/or to make it possible that the constructs can more easily assume a desired spacial conformation or arrangement of the various components present therein). Again, these are advantages that may not or not easily be provided through the use of a spherical or particulate carrier.

In a further embodiment, the invention comprises a protein construct that comprises at least two proteins, peptides, factors, subunits or other compounds that are linked to (and, therefore, linked to (and are linked to each other via)) a polymeric backbone as described herein.

The invention further relates to methods for providing protein constructs that comprise linking at least one, and preferably as least two, proteins, peptides, factors, subunits or other components (as described herein) to a pharmaceutically acceptable helical polymer as described herein.

The invention further relates to the use of a pharmaceutically acceptable helical polymer in protein constructs and/or in the preparation of protein constructs, and, in particular, of the protein constructs described herein.

The invention further relates to the composition that comprises at least one construct of the invention. Such a composition may, in particular, be a pharmaceutical composition that comprises (next to the construct(s) of the invention) at least one pharmaceutically acceptable excipient, carrier or diluents.

The invention also relates to a construct of the invention (or a pharmaceutical composition comprising the same) for use in therapy, in particular, in immunotherapy, such as in immunotherapy of cancer.

The invention also relates to a method for inducing, enhancing or suppressing an immune response by a T-cell, which method at least comprises a step of contacting the T-cell with a construct of the invention (or a pharmaceutical composition comprising the same). This method may be performed in vitro, ex vivo or in vivo. When it is performed in vivo, the method of the invention usually comprises administering a construct of the invention (or a pharmaceutical composition comprising the same) to the subject to be treated.

The invention also relates to a method for inducing, enhancing or suppressing an immune response against an antigen, which method at least comprises a step of contacting at least one T-cell with an antigen-presenting construct of the invention that comprises the antigen (or one or more suitable parts, fragments, epitopes or antigenic determinants of the same) or with a pharmaceutical composition comprising the same). This method may be performed in vitro, ex vivo or in vivo. When it is performed in vivo, the method of the invention usually comprises administering the construct of the invention (or a pharmaceutical composition comprising the same) to the subject to be treated. The method can, for example, be used for immunotherapy of cancer, in which case, the antigen will be a tumor antigen expressed by the tumor to be treated. Suitable doses and dosing regimens for such treatment can be suitably chosen by the clinician, based on the tumor to be treated and the construct used. Such treatment can, for example, be applied after procedures that reduce tumor burden, such as surgery and chemotherapy, when tumor load is low, but there still is a high risk of recurrence of the disease. In this setting, treatment with the constructs of the invention that comprise one or more tumor antigens or tumor antigenic peptides might be an effective way to induce anti-tumor immune responses, which prevent recurrent disease.

Anti-cancer immunotherapy is a promising approach that aims at inducing highly specific cellular responses against cancerous cells. Multiple preclinical and clinical studies have exploited dendritic cells (DCs) to evoke tumor antigen-specific immune responses. DCs are key antigen-presenting cells (APCs) due to their superior ability to take up, process and present antigens (derived from pathogens or tumors) to T-cells, resulting in efficient immune responses. Most DC vaccines consist of ex vivo-generated autologous monocyte-derived DCs loaded with tumor antigens. While effectivity has been demonstrated in some patients, it requires expensive, time-consuming GMP culturing for each individual patient. Furthermore, the quality and quantity of autologous DCs is often impaired in advanced cancer patients. The invention solves these issues by providing the constructs described herein, which can be used as a synthetic APC/DC, with T-cell stimulating capabilities similar to natural-occurring DCs, as a general applicable system for in vivo stimulation of antigen-specific T-cells. While the artificial APCs described in the art are based on a spherical-shaped backbone, the invention uses a filamentous-shaped polymer with unique chemical, physical and biological properties as backbone. Some advantageous features of this backbone are that it displays large flexibility and intrinsic motility. This has potential advantages for the biodistribution, migratory capacity and efficient cross-linking of receptors on the T-cell surface, which should provide the filamentous-shaped synthetic-DCs of the invention with superior in vivo T-cell-stimulating capacities compared to spherical-shaped synthetic DCs. Different modules (i.e., MHC/peptide complexes, co-stimulatory signals) can be easily attached to the polymer backbone, thereby creating a "plug and play" system offering a great flexibility for incorporation of a variety of stimuli. This system offers the possibility to determine the optimal stimuli for efficient T-cell activation and to investigate the influence of shape and flexibility of the synthetic-DCs. In this way, the invention provides to the skilled person an effective, customizable, off-the-shelf system for cancer immunotherapy, circumventing the disadvantages of using autologous DCs.

Cellular cancer immunotherapy generally aims at inducing or enhancing anti-tumor immune responses in cancer patients. Manipulation of this response can be accomplished by dendritic cell- (DC-) based immunotherapy. DCs play a key role in anti-cancer immune responses, as they are better equipped than other antigen-presenting cells (APC) to efficiently activate naive T-cells. DCs are widely distributed in all tissues where they phagocytose antigens from different origin. After uptake, the antigens are processed and presented in the context of MHC molecules (MHC/peptide complex) on the surface of the DCs. Upon appropriate stimulation, the DCs undergo further activation and migrate to the secondary lymphoid organs, where they present the antigen to T-cells and induce an antigen-specific immune response. Therefore, DCs are a potent target cell for immunotherapeutic strategies.

A widely used DC-based strategy is ex vivo generation of DCs from autologous blood-derived monocytes and subsequent loading with antigenic peptides. Upon reinfusion into the patient, these DCs are able to migrate to the lymph nodes and induce antigen-specific T-cells. This strategy for DC-based immunotherapy has been proven in multiple experimental clinical trials.

However, this strategy requires expensive (GMP/GLP) and time-consuming customized isolation and culturing of monocyte-derived DCs for individual patients, which limits its general application. Furthermore, the DCs of cancer patients are highly variable in quantity and quality due to immunosuppressing factors associated with tumor growth, and often have impaired capabilities of antigen uptake, motility and T-cell activation. Accordingly, the invention provides an alternative and improved approach, offering easy assemblage, flexibility and broad applicability using an entirely synthetic dendritic cell, which circumvents the use of autologous DCs and, which, therefore, as these "synthetic" DCs have a synthetic nature, is not affected by the immunosuppressive tumor environment, and can also be used for large numbers of patients.

The synthetic DCs described herein can also be designed to have or combine several functionalities, such as a T-cell address allowing targeting of antigen-specific T-cells, T-cell activation signals, and preferentially signals that either attract T-cells or preferentially brings the synthetic DC to lymph node areas; and/or some of the further properties and functionalities mentioned herein.

Also, the constructs of the invention, by exploiting a flexible filamentous-shaped, instead of a rigid spherical-shaped, backbone, provide additional advantages relating to biodistribution related to shape, potential cross-linking of receptors on the T-cell upon binding of the synthetic DCs and optimal mimicking DCs by controlled generation of nano-domains/modules supporting different functions and aimed at optimal stimulation of T-cell function.

The helical polyisocyanide polymers that are preferably used as backbone for the generation of the synthetic DCs described herein have several advantageous properties. These strong polymer chains with a diameter of only about 2 nm and lengths up to 3 µm can be synthesized and adopt a well-defined helical structure in solution. The preferred polyisocyanides may contain alanine side chains or other side chains derived from the amino acids used in the polymerization that may stabilize the helical structure via the formation of a hydrogen bonding network. The introduction of ethylene glycol units to the alanine side chains increases water solubility. Different components can be coupled to the polyisocyanide backbone via reactive groups attached to the ethylene glycol. Another advantage of the polyisocyanide backbone is its intrinsic motile behavior (reptation-like motion), that strongly resembles the migratory behavior of DCs and is responsible for the extremely dynamic and flexible nature of the constructs of the invention. Due to these "reptation-like" motions, the polyisocyanide backbone has migratory capacity, in contrast to the static and rigid spherical-shaped backbones. This intrinsic motility can potentially be exploited to guide the synthetic DCs toward T-cell-rich areas, such as the secondary lymphoid organs.

The art describes several artificial APCs, which are based on spherical-shaped structures as backbone (i.e., magnetic beads, latex beads, poly(lactic-co-glycolic acid) (PLGA) microparticles) (Steenblock et al., *Expert Opin. Biol. Ther.* (2009) 9:451-464). These known artificial APCs have so far almost exclusively been used for ex vivo stimulation and expansion of autologous T-cells and reinfusion of these T-cells in the patient (see, for example, Chang, *Exp. Mol. Med.* (2006) 38:591-598; Lu et al., *Cancer Immunol. Immunother.* (2009) 58:629-638; Oelke et al., *Nat. Med.* (2003) 9:619-624; and Zhang et al., *J. Immunol.* (2007) 179:4910-4918). By contrast, in addition to these known ex vivo applications, the constructs of the invention can (also) be used for in vivo stimulation of antigen-specific T-cells.

When the constructs of the invention are to be used as such "synthetic DC constructs," their design and production will generally involve one or more of these signals, which are essential for efficient DC T-cell interactions and subsequent T-cell activation. As is known in the art, generally, at least two signals are required for efficient activation of naive T-cells by DCs. First, the antigen-specific signal that is provided via binding of the T-cell receptor to the MHC/peptide complex on the DC. Additionally, an antigen non-specific signal, provided by the ligation of so-called co-stimulatory molecules (i.e., CD28, 4-1BB) on DC and T-cell, provides a second signal. DCs up-regulate the expression of co-stimulatory molecules upon activation by danger signals. The expression of co-stimulatory molecules, allows the DCs to induce proper activation of naive T-cells. Thus, the "synthetic DC" constructs of the invention most preferably contain (or can provide to a T-cell) one or more antigen-specific signals provided by MHC/peptide complexes and one or more co-stimulatory signals provided by agonists against co-stimulatory molecules, such as CD28.

A further important feature of the artificial APCs of the invention is their capacity (similar to natural DCs) to migrate to the lymph nodes where the activation process of T-cells is located. This directed migration is propelled by a complex motility machinery and sensing devices (chemokine receptors) at the cell surface. This migratory capacity can be regarded as a third feature/signal that could be included in the synthetic DC constructs of the invention, for example, by including components such as chemokines such as CCL-19 or CCL-21 or also cytokines such as IL-12.

The different components can be coupled to the polymeric backbone via reactive groups, thereby creating a synthetic DC construct, which exploit the advantages provided by the use of a flexible filamentous-shaped backbone instead of a rigid spherical-shaped carrier, such as: (i) the (improved) dynamic and migratory behavior of the synthetic DC constructs; (ii) potential cross-linking of receptors on the T-cell upon binding of the synthetic DC constructs; and (iii) their biodistribution.

In addition, compared to the artificial APCs described so far in the art, which are based on spherical-shaped structures as backbone (i.e., magnetic beads, latex beads, poly(lactic-co-glycolic acid) (PLGA) microparticles), the use of a filamentous-shaped structure as backbone may also persist significantly longer in the circulation than spherical-shaped structures upon injection in rodents (see, for example, Geng et al., *Nat. Nanotechnol.* (2007) 2:249-255). Long circulation times of the synthetic DC constructs of the invention might be of particular importance for efficient in vivo T-cell activation. Furthermore, microparticles between 4-10 microns, a similar size as T-cells, provide optimal T-cell stimulation, while nanoparticles are much less efficient (see, for example, Mescher, *J. Immunol.* (1992) 149:2402-2405, and Steenblock and Fahmy, *Mol. Ther.* (2008) 16:765-772). Also, systemically administered micron-sized non-deformable particles form a major health risk as they can cause embolic complications (see, for example, again Geng et al., *Nat. Nanotechnol.* (2007) 2:249-255). Generally, the constructs of the invention may also provide the advantages that are associated with the use of "nano-sized" particles compared to "micron-sized" particles (see, for example, Cruz et al., *J. Control. Release* (2010) 144(2):118-126).

For the purposes of the invention, one extremely dynamic and flexible filamentous-shaped backbone can be assembled by the polymerization of isocyanides to provide polyisocyanides. Such polyisocyanides have several unique properties (see, for example, Metselaar et al., *Chemphyschem.* (2007) 8:1850-1856; and Metselaar et al., *Chemistry* (2007) 13:950-960). Polymer chains with a diameter of only 2 nm and lengths up to 3 μm can be synthesized and adopt a well-defined helical structure in solution. The polyisocyanide contains alanine side chains that stabilize the helical structure via the formation of a hydrogen bonding network. Different components can be coupled to the polyisocyanide backbone via reactive groups attached to the side chains, so as to provide a "plug and play" system that offers great flexibility over the assembly of the different modules of the synthetic DC constructs. The constructs generated in this way are easy modifiable and different combinations and ratios of ligands can be incorporated.

Thus, the components (or "modules") can be attached to the backbone (optionally via the side chains and/or using suitable spacers or linkers) in a way that will permit varying and controlling intermodule distance and placement. This can, for example, be performed using the so-called "click" chemistry (see, for example, Kitto et al., supra, and some of the other references on functionalizing helical polymers mentioned above), the design of the synthetic DCs can be controlled in several ways (or any suitable combination thereof):

By controlling the spacing of the modules: modules can be provided at specific distances of each other by mixing monomers containing reactive groups with unfunctionalized monomers in a ratio of 1:10 or 1:50 or 1:100 during assembly of the polyisocyanide backbone. Following this approach, when coupling modules to the reactive groups, they can, for example, be positioned every 1 nm/5 nm/10 nm, respectively. This approach will allow statistical control over the intermodule distance.

By controlled coupling of multiple types of modules: for example, three different protection groups on the backbone that shield the reactive groups can be used to couple, for instance, three different modules (i.e., MHC/peptide complexes, co-stimulatory modules, chemokines). By stepwise removal of each protection group and subsequent addition of the desired module, multiple modules can be coupled to the backbone.

Alternatively, by using monomers containing different reactive groups (i.e., maleimide, NH-esters and biotin), that each bind a specific module, different modules can be attached simultaneously.

By controlling the placement of different modules: monomers containing different reactive groups (i.e., maleimide, NH-esters, biotin) can also be used to create synthetic DCs with, for instance, module A at the front of the polymer, module B along the whole polymer, and module C at the end of the polymer. By adding the monomers containing the different reactive groups (each coupling a specific module) at different time points during the polymerization process, the placement of different modules on the synthetic DCs can be controlled.

With advantage, the design and production of the constructs of the invention can be "modular" so as to allow easy linking, modification, addition of different modules and changing the density and intermodule distance. Each of the components of the construct (i.e., each "module") can be directly attached to the backbone or, for example, via streptavidin (SAv). Coupling of SAv to the backbone enables easy attachment of different biotinylated modules. On the other hand, direct coupling can permit varying intermodule distance and placement, so as to provide for an optimal combination, density, intermodule distance and placement of the different components for induction of efficient antigen-specific T-cell responses.

Figure 2:
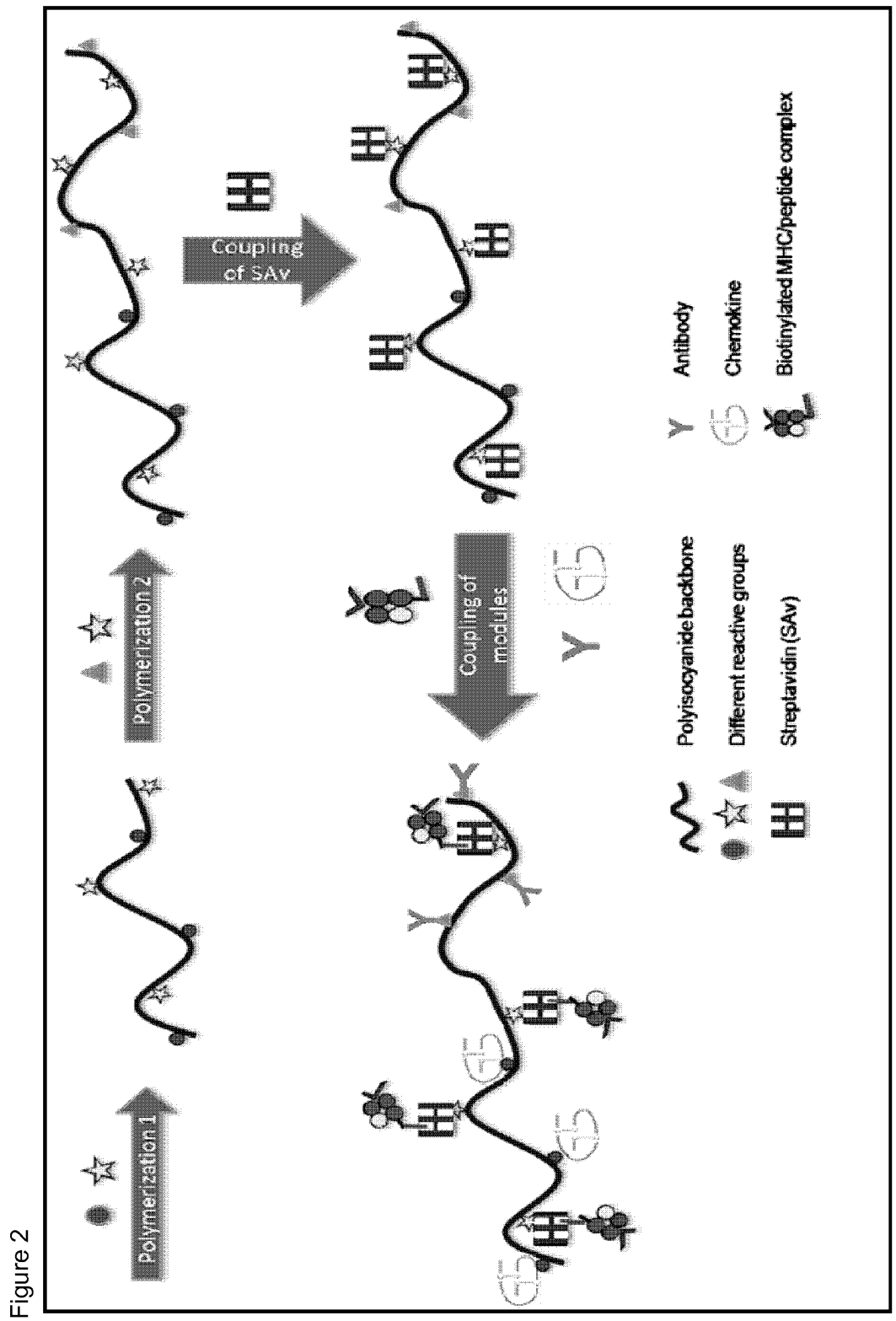
FIG. 2 is a schematic view showing one methodology for attaching functional groups to a helical polymeric backbone.

By means of illustration only, the non-limiting FIG. 2 schematically shows one way that a helical polymeric backbone can be provided with different functional groups (indicated by the small circles, stars and triangles), also through modular assembly ("Polymerization 2"), whereupon the different functional groups can then be used for attachment of different proteins, peptides or other components (for example, MHC complexes, antibodies and chemokines, as shown in FIG. 2), either through direct covalent linkage (as shown for the antibodies and chemokines) or via formation of a binding pair (as shown for the MHC complexes, which are bound to the backbone via the formation of a biotin/streptavidin binding pair).

Thus, for example, MHC/peptide complexes and different agonistic antibodies against T-cell co-stimulatory molecules (i.e., CD28, 4-1BB, OX-40, LFA-1) can be suitably linked to the helical polymeric backbone. In addition, to guide synthetic DC constructs to the secondary lymphoid organs in vivo, the intrinsic motility and random biodistribution of the backbone can be exploited, optionally in combination with, for example, an antibody or antibody fragment against an endothelial adhesion molecule selectively expressed in the lymph nodes (i.e., VAP-1 or PNAd23). Thus, in this way, lymphoid endothelial address signals (i.e., antibodies directed against lymphoid endothelial adhesion molecules such as VAP-1 or PNAd23) can be included in the constructs of the invention to guide synthetic DCs to the T-cell areas of the secondary lymphoid organs; and as already mentioned, optionally, also chemokines can be included to attract naïve and memory T-cells. Alternatively, the constructs of the invention may also be directly injected in the lymph nodes of the patients (intranodal injection).

The interactions between such synthetic DC constructs and T-cells and receptor cross-linking upon binding can, for example, be visualized by live imaging techniques, and the motility and migratory capacity of the synthetic DC constructs can be analyzed on a 3-D extracellular collagen matrix (see, for example, the techniques described by Gunzer et al., *Adv. Exp. Med. Biol.* (1997) 417:97-103; and by Gunzer et al., in *Immunity* (2000) 13:323-332).

Another remarkable feature of such helical polymeric backbones (and, in particular, of the polyisocyanide backbone referred to herein) is that it displays intrinsic motility (so called reptation-like motion), which is responsible for its dynamic and migratory capacity. Due to the reptation-like motions, the polyisocyanide backbone is extremely dynamic and flexible, in contrast to the static and rigid spherical-shaped backbones. This should also allow the synthetic DC constructs to efficiently cross-link receptors and molecules on the T-cell surface. Furthermore, the intrinsic motility of the polyisocyanide backbone can potentially be exploited to direct the synthetic DC constructs towards T-cell-rich areas such as the secondary lymphoid organs. Thus, the use of the flexible filamentous-shaped backbone (instead of a rigid spherical-shaped carrier) in the synthetic DC constructs of the invention could provide a number of advantages in terms of biodistribution, in vivo toxicity and the efficient cross-linking of T-cell receptors.

In summary; the invention relates to the use of worm-like polymers in the treatment of a variety of immune disorders. It also relates to the diagnostic use of such polymers. In this latter case, the polymers preferably carry a detectable label attached to a reactive group on the polymer.

As described herein, the polymer is flexible and able to "follow" the clustering of T-cell receptors when the cells form the so-called immunological synaps, unlike antigens coupled to bead-like scaffolds. The stiffness of the polymer precludes the polymer from forming an intricate tangle.

The stimulation of T-cells by the polymers is based upon T-cell receptor engagement with the polymer loaded with antigen and co-stimulatory molecules attached to the filamentous polymer or any compound that mimics antigen and co-stimulatory molecules to fully stimulate T-cells.

The induction of tolerance is based on providing only the antigenic stimulus (without co-stimulus): induction of T-cell anergy. This is of importance where tolerance has to be induced like autoimmune diseases and grafting organs from allogeneic donors.

With regard to imaging, it should be realized that, based on the marvelous tissue-penetrating characteristics of the polymer, the polymer can be targeted to the cell of choice after coupling an address label to it, for example, a monoclonal antibody that targets a selected cell type based on unique expression of the target molecule by that cell. Any imaging compound can be coupled to the polymer. For example, luciferase, radioactive epitopes, MRI-enhancing compounds, fluorescent dyes, etc.

It is also possible to target drugs or prodrugs. Using the same targeting strategy as above, namely, delivering the polymer by means of an antibody or other compounds that bind to target cells. In this case, a drug or prodrug can be coupled to the polymer. The prodrug will be converted into the active drug after cell penetration.

The invention will now be demonstrated by means of the non-limiting Experimental Part below and the appended non-limiting Figures, which show:

EXPERIMENTAL PART

Example 1: Coupling of Components to the Helical Polyisocyanide Backbone

Anti-CD3 antibodies were attached to the helical polyisocyanide backbone as a simplified mimic for T-cell receptor stimulation. The anti-CD3 antibodies were coupled to the backbone via biotin-streptavidin binding.

The helical polyisocyanides were made more water-soluble by attaching polyethylene glycol (PEG) to the alanine side groups. Reactive groups (NHS-esters) were introduced at the end of part of the PEG chains, creating functionalized polysiocyanides. Subsequently, the functionalized polyisocyanides are reacted with streptavidin to obtain streptavidin-functionalized polyisocyanides. To remove the unbound streptavidin, the polyisocyanides were dialyzed against phosphate-buffered saline (PBS) for several days, using a 300 kDa cellulose ester membrane. The protein and polymer concentrations were analyzed to determine the amount of streptavidin bound to the polyisocyanides (analyzed by Coomassie blue staining and CD spectroscopy, respectively). Anti-CD3 antibodies were biotinylated using sulfo-NHS-LC-biotin. Subsequently, the biotinylated anti-CD3 antibodies were mixed with the streptavidin-functionalized polyisocyanides. The solution was incubated for one hour to allow binding of the biotinylated anti-CD3 antibodies to the streptavidin on the polyisocyanides. To remove unbound anti-CD3 antibody, the polyisocyanides were dialyzed against PBS for several days, using a 300 kDa cellulose ester membrane. The protein and polymer concentration was analyzed to determine the amount of anti-CD3 antibody attached to the polyisocyanides. The obtained anti-CD3 containing polyisocyanides were used in Example 5.

Figure 3:
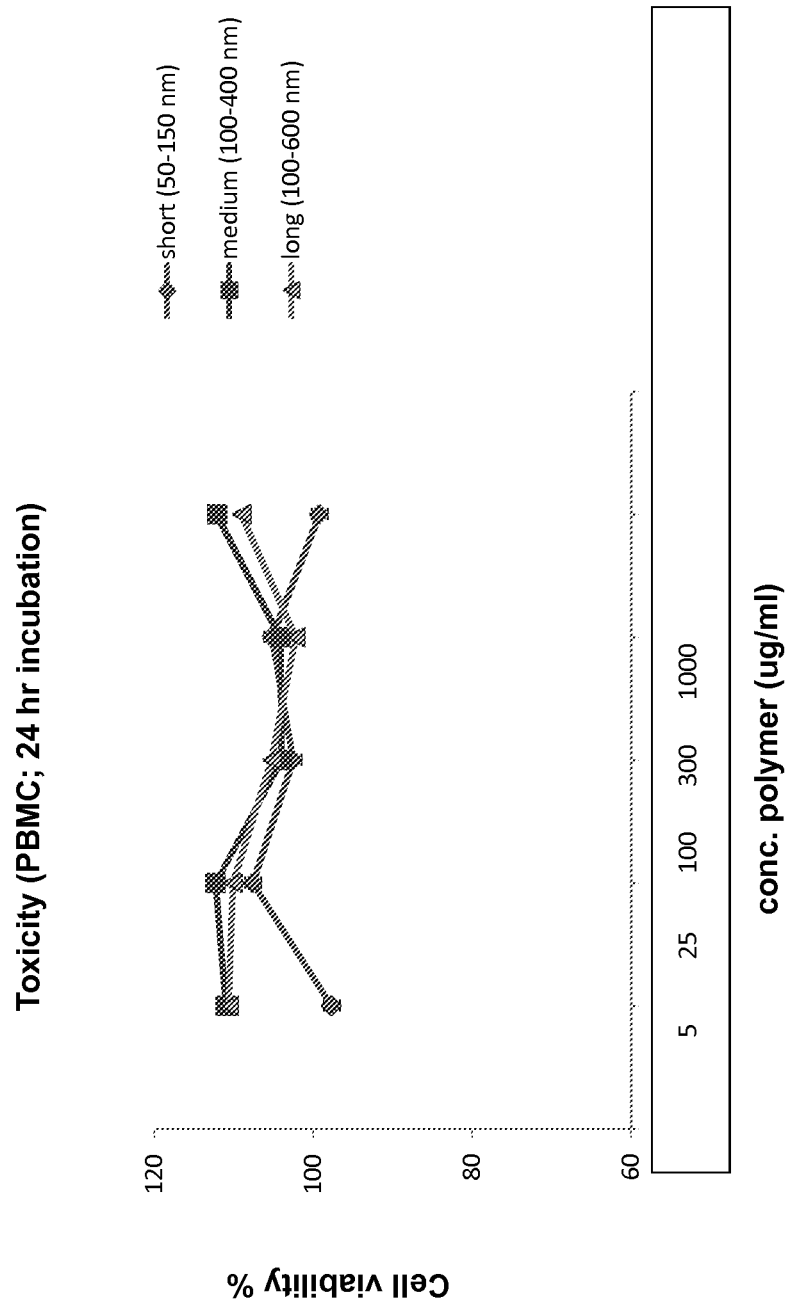
FIG. 3 is a graph showing the results from in vitro proliferation toxicity assay. Peripheral blood mononuclear cells (PBMCs) were incubated with different concentrations of polyisocyanides (of different lengths) for 24 hours. Subsequently, the cell viability was determined by annexine-V/PI staining.
Figure 4:
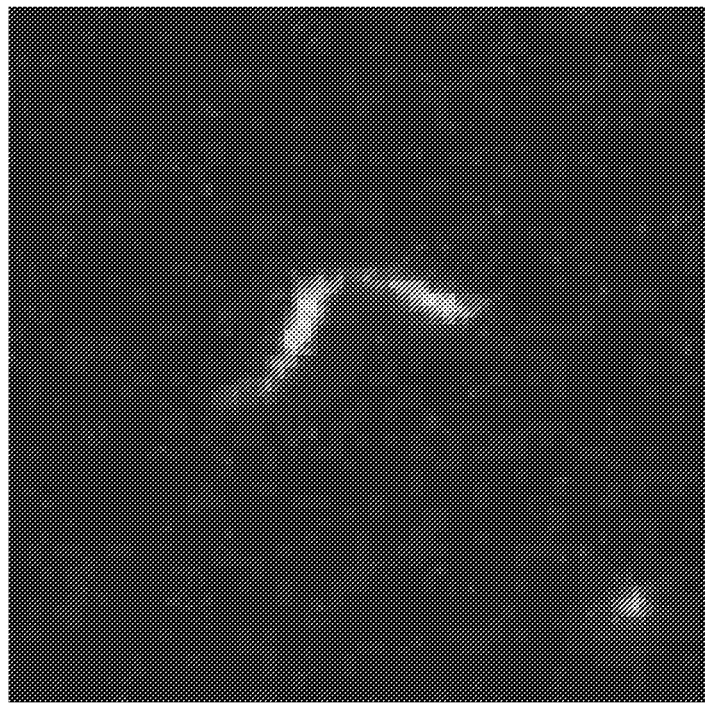
FIGS. 4A to 4D are snapshot pictures taken at different time points from a movie taken of a polymeric backbone suitable for use in the invention in a physiological salt solution using confocal microscopy techniques.
Figure 4:
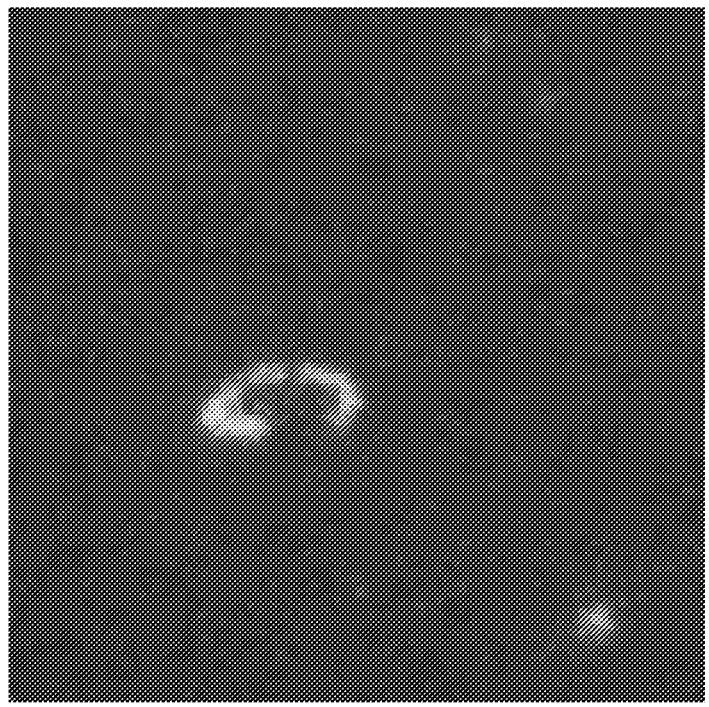
Figure 4:
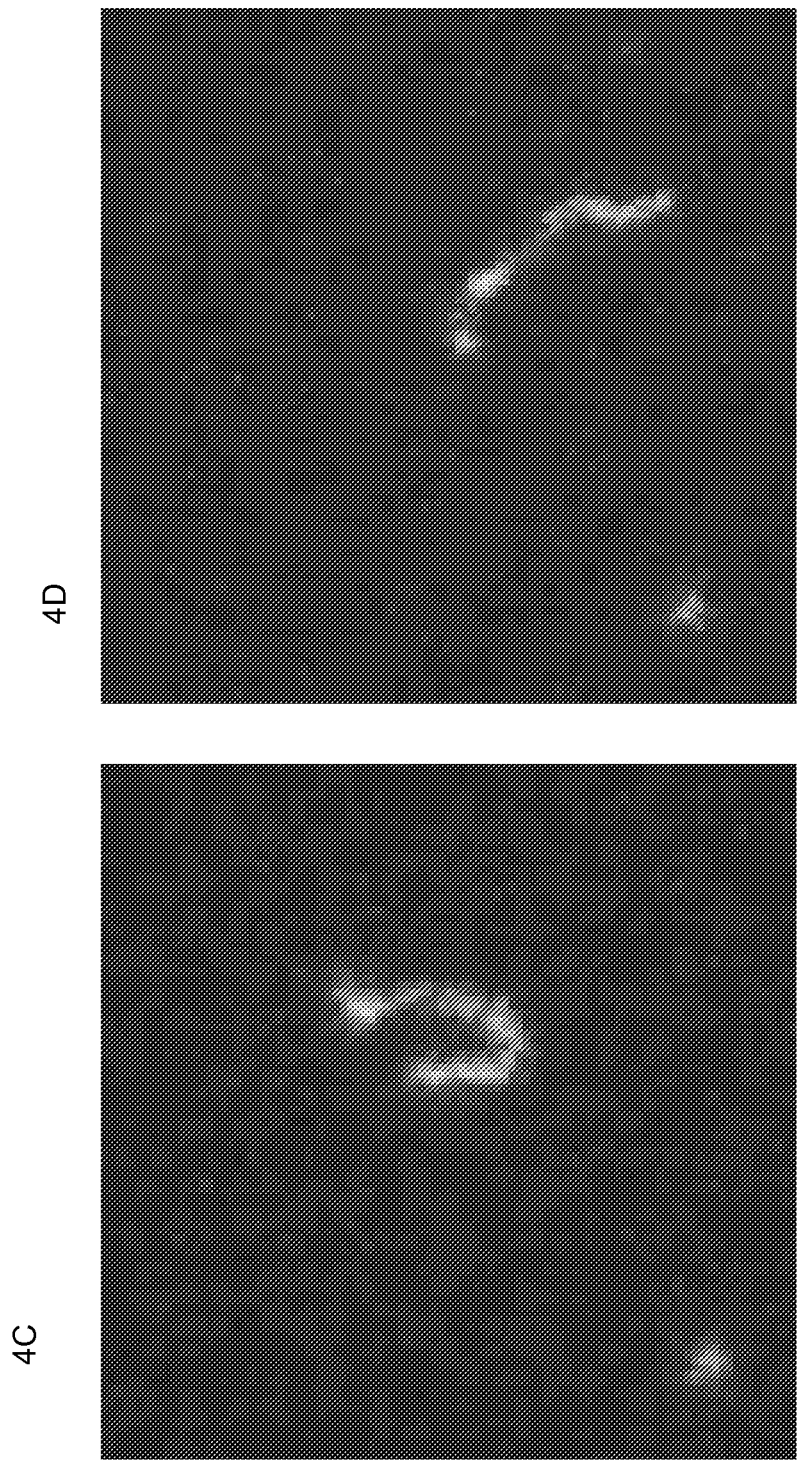

Example 2: The Polyisocyanide Backbone does not Display Toxicity In Vitro and In Vivo Toxicity in vitro: peripheral blood mononuclear cells (PBMCs) were incubated with different concentrations of polyisocyanides (of different lengths) for 24 hours. Subsequently, the cell viability was determined by annexine-V/PI staining. The results are shown in FIG. 3.

In vivo toxicity was determined by i.v injection of different amounts of polyisocyanides (100 µg and 1 mg) in C57/B16 mice. The mice showed no signs of toxicity.

Example 3: Motility of the Polymeric Backbone

By using fluorescent microscopy and live imaging techniques, it was shown that a filamentous-shaped backbone displays intrinsic motility, resulting in great flexibility and motility. FIGS. 4A to 4D show snapshot pictures taken at different time points from a movie taken of the backbone in a physiological salt solution using confocal microscopy techniques.

Example 4

Before exploring in vivo T-cell activation, the in vivo biodistribution of the synthetic DCs based on a helical polymeric backbone was assessed. For this, diethylenetriamine-pentaacetic acid (DTPA), a chelating agent for indium-111, was coupled to the synthetic DCs. The biodistribution and circulation time of synthetic DCs, containing different modules, were analyzed by measuring indium-111 activity upon injection in mice. It was demonstrated that the indium-111-labeled filamentous-shaped backbone nicely distributes over the organs upon systemic administration in mice (as measured 30 minutes after i.v. injection; data not shown). The polyisocyanide backbone was even found back in the secondary lymphoid organs (spleen and lymph nodes), which might be important for effective T-cell activation.

Figure 5A:
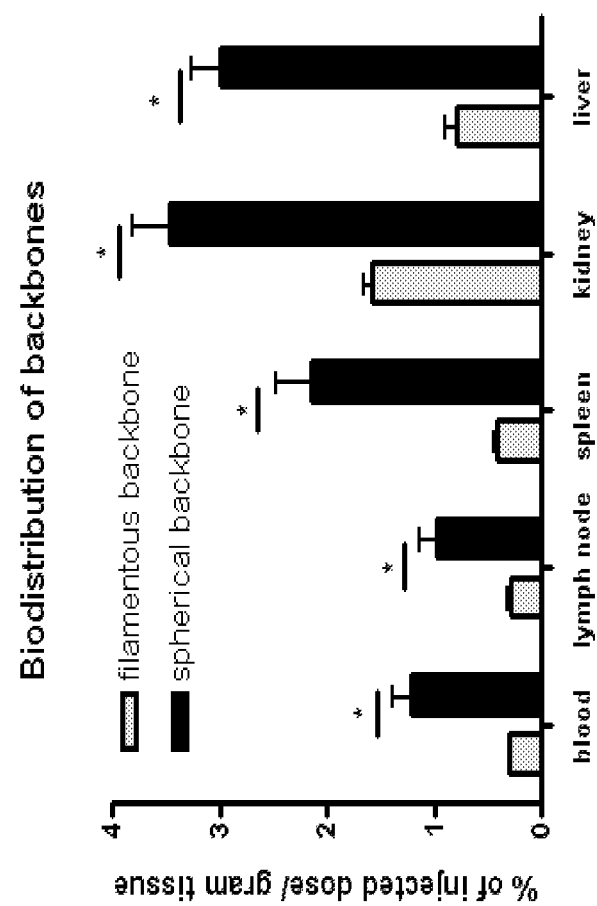
FIGS. 5A and 5B are graphs showing the accumulation of the filamentous polyisocyanide backbone in several organs measured 24 hours after i.v. injection and the persistances in the circulation compared to a spherical backbone, measured 30 minutes after i.v. injection.
Figure 5B:
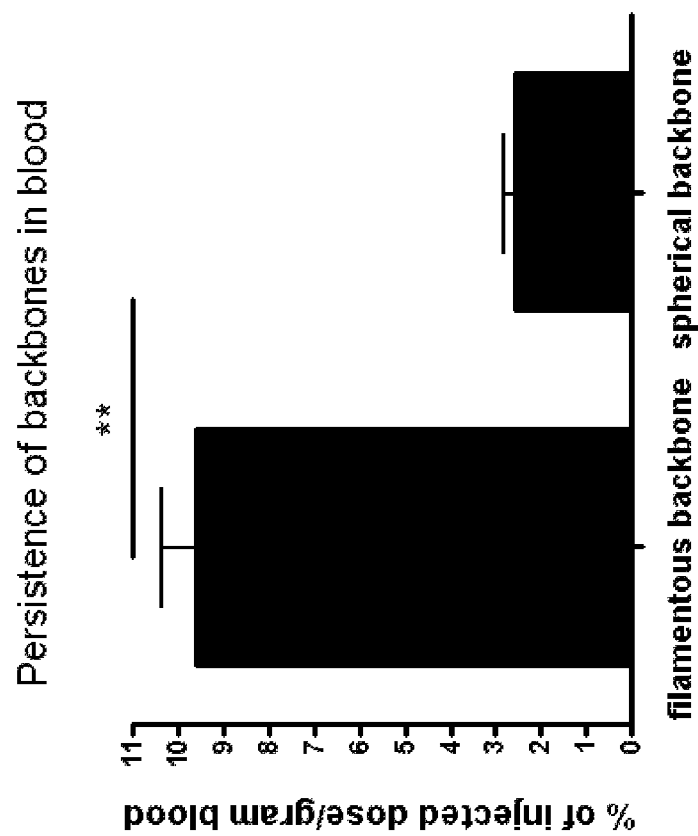

Furthermore, it was established that the filamentous polyisocyanide backbone shows a higher accumulation in several organs (FIG. 5A; measured 24 hours after i.v. injection) and persists in higher amounts in the circulation compared to a spherical backbone (FIG. 5B; measured 30 minutes after i.v. injection).

Example 5

Figure 6:
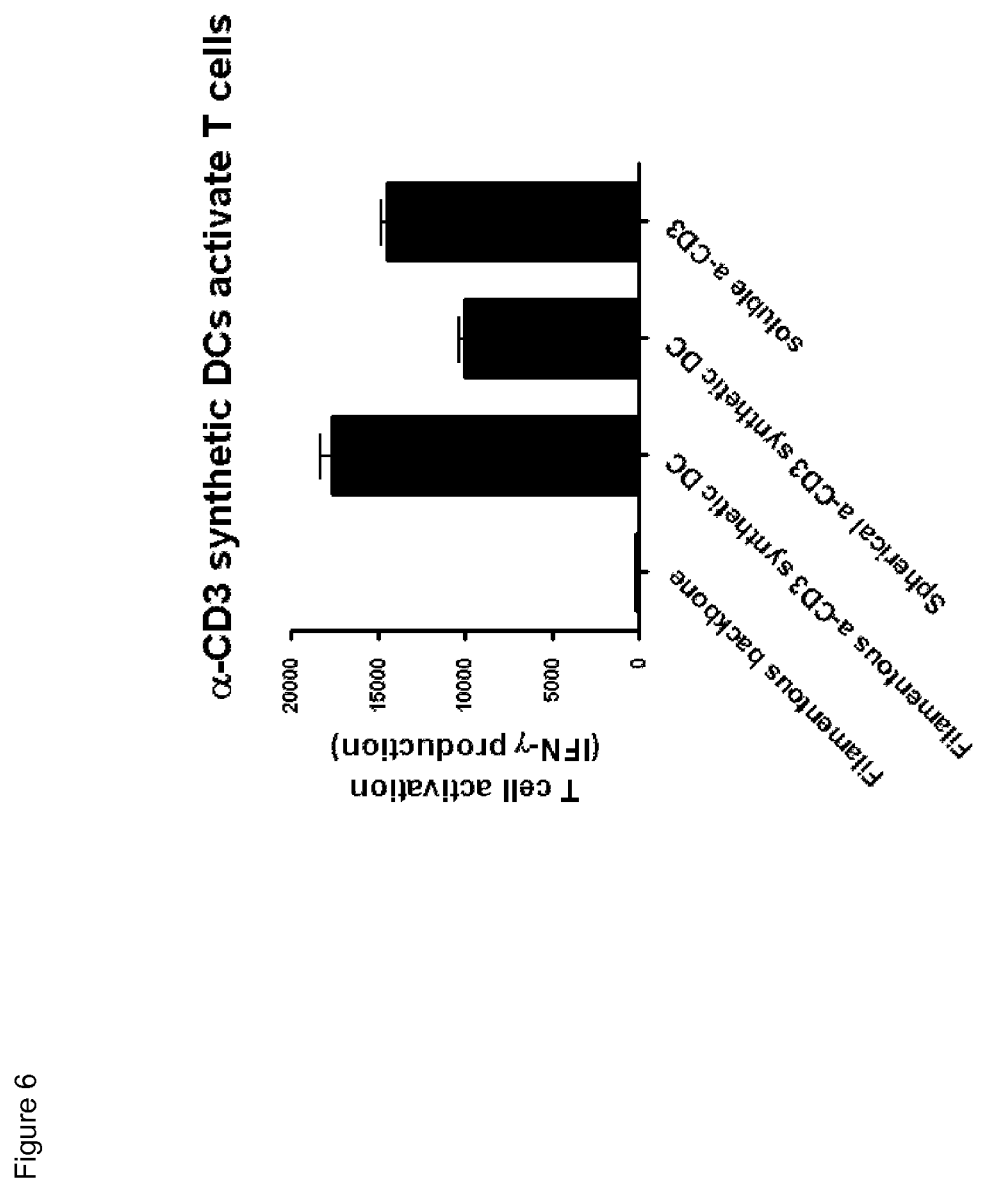
FIG. 6 is a graph showing the results obtained in Example 6, demonstrating that α-CD3 synthetic DCs bind and activate peripheral blood lymphocytes (PBLs), as measured by the induction of IFN-γ production.
Figure 7:
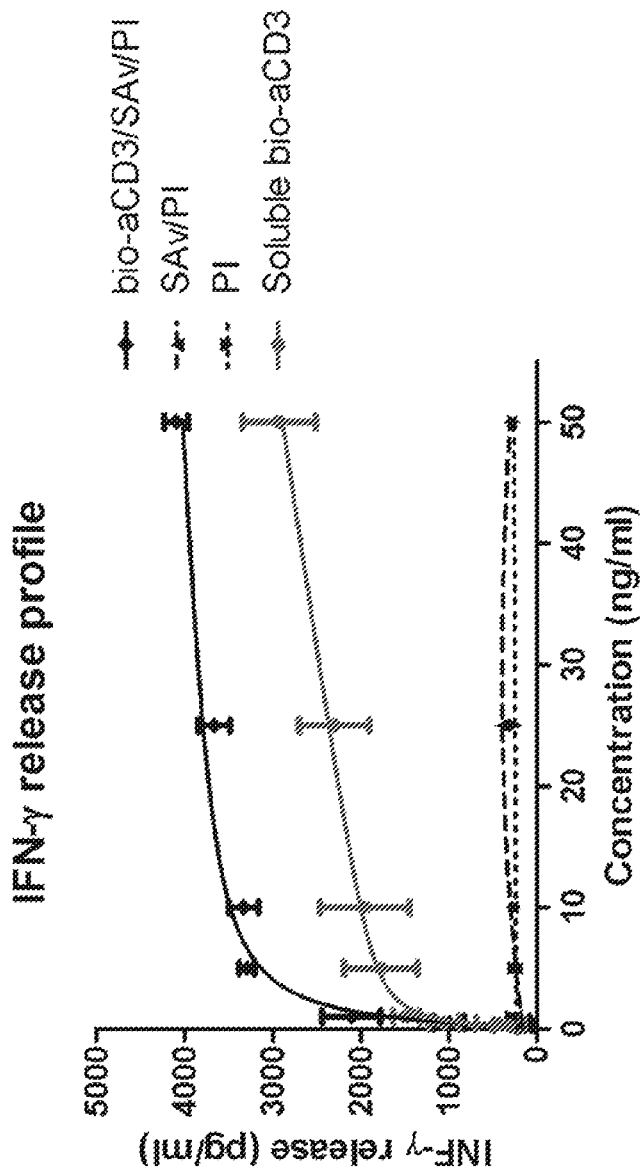
FIG. 7 is a graph showing interferon gamma release profile. Say-polymers, streptavidine coupled to the linear polymer; α-CD3 polymers, biotinylated monoclonal antibody to CD3 bound to streptavidine-coupled polymers; SavPLGA, strepavidine coupled to PLGA beads; α-CD3 PLGA, biotinylated monoclonal antibody to CD3 bound to streptavidine-coupled PLGA beads; soluble α-CD3, monoclonal antibody directed to CD3. IFN-γ concentration is expressed in pg/ml.
Figure 8:
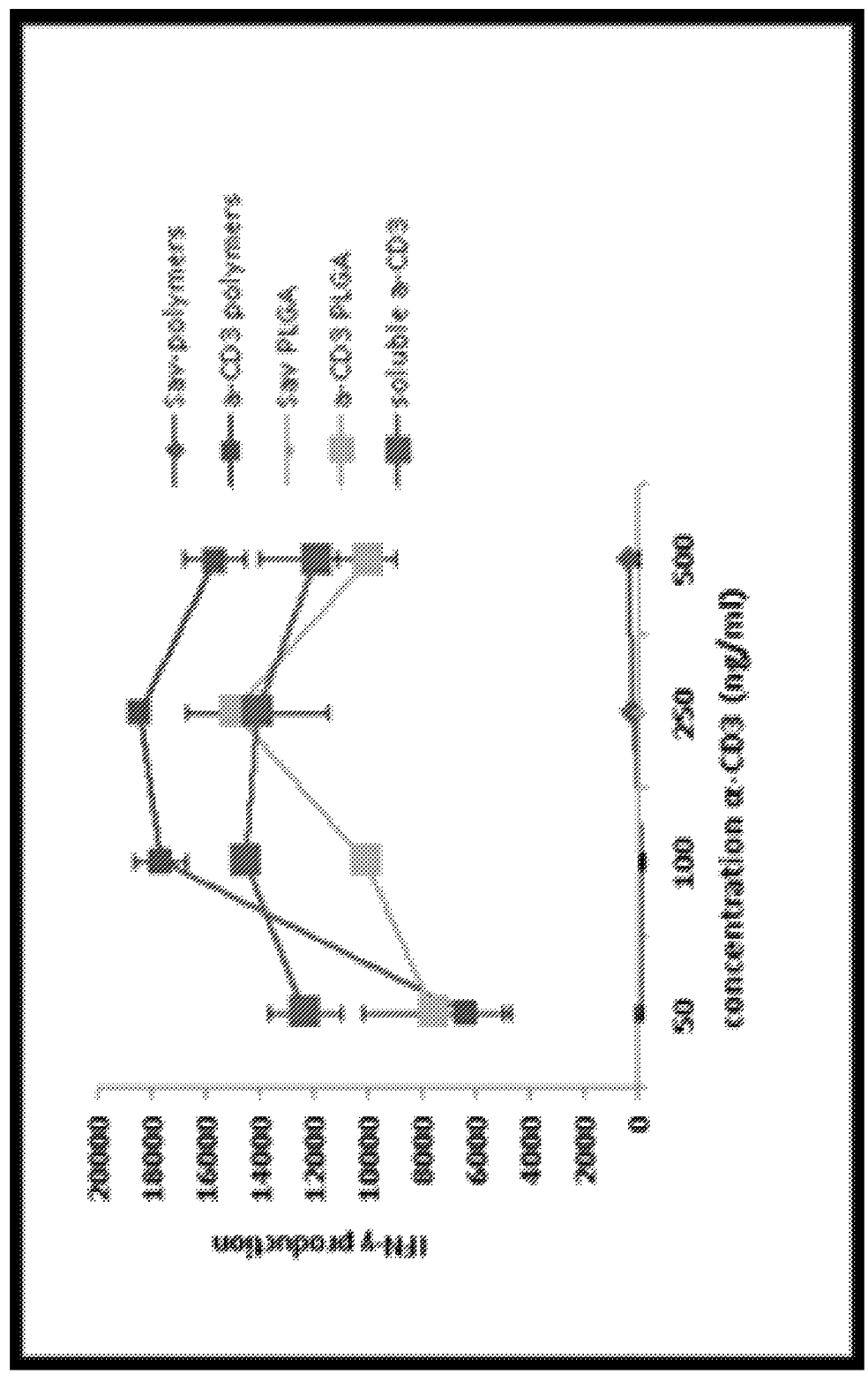
FIG. 8 is a graph showing interferon gamma production. Bio-αCD3/Sav/Pl, biotinylated monoclonal antibody to CD3 bound to streptavidine coupled to the linear polymer; Sav/Pl, streptavidine coupled to the linear polymer; Pl, linear polymer; soluble bio-αCD3, biotinylated monoclonal antibody directed to CD3.
Figure 9:
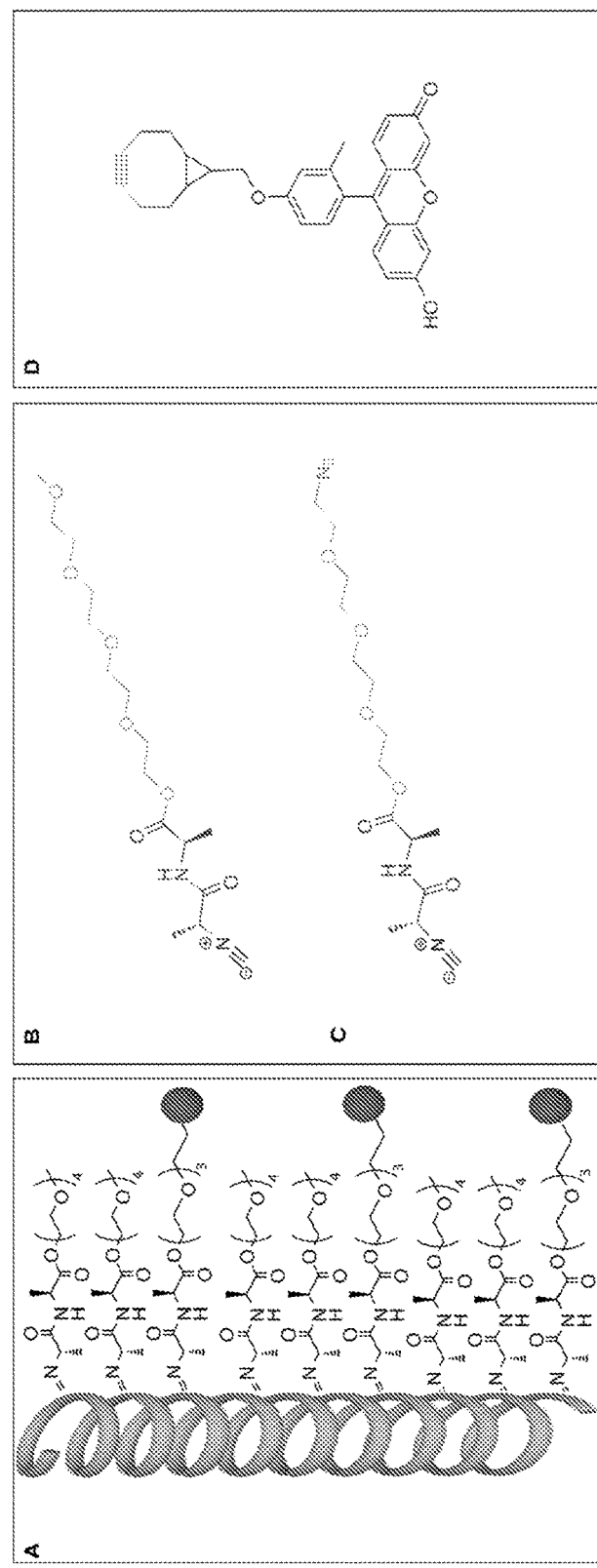
FIG. 9 depicts Scheme 3. Chemical structure of A) the "worm-like polymer" (R side chains defined by B and C), B) the predominant isocyanide monomer, C) azide functional monomer. Monomers B and C comprise from the left to the right: isocyanide partpeptide part; (water-compatible) polyethyleneglycol part. C contains an azide functional group at the end of the molecule. This may also be substituted with acetylene-containing extensions for click reaction, maleimide, NHS ester, or any other group that can be used for bioconjugation. D) TokyoGreen (fluorescein part).

Biotinylated anti-CD3 antibodies (α-CD3) were attached to an SAv-conjugated backbone (α-CD3 synthetic DC), in the manner described in Example 1, to provide a mimic for T-cell receptor stimulation. It was confirmed that these α-CD3 synthetic DCs bind and activate peripheral blood lymphocytes (PBLs), demonstrating that this system is indeed feasible. α-CD3 attached to the filamentous-shaped backbone induces a comparable IFN-γ production as soluble α-CD3. The results are shown in FIG. 6.

Example 6

For analyzing in vivo T-cell activation, H2-Kb/OVA monomers will be used. Synthetic DCs, containing H2-Kb/OVA monomers and different T-cell activation modules, are injected in mice. CFSE-labeled OVA-specific T-cells from OT-1 transgenic mice (available at host laboratory) will be co-injected and OVA-specific T-cell proliferation and IFN-γ production will be analyzed. T-cell activation upon injection of synthetic DCs via different routes will be investigated (i.v., footpad, s.c). Furthermore, in vivo killing assays are performed to analyze whether the activated T-cells are effective. Finally, tumor growth studies are done to investigate if T-cells, activated by the synthetic DCS, are capable of eliminating tumors. For this, mice are inoculated with an immunogenic (B16/OVA) or a non-immunogenic (MCA/sOVA) OVA-expressing tumor and subsequently injected with synthetic DCs.

Example 7

To investigate in vitro antigen-specific T-cell activation upon stimulation with synthetic DCs, HLA-A2 monomers containing an epitope of the melanoma-associated tumor antigen gp100 (HLA-A2/gp100) are used. Antigen-specific T-cell stimulation is assessed by culturing synthetic DCs, containing HLA-A2/gp100 monomers, with gp100-specific T-cells. Gp100-specific T-cells are generated by electroporating RNA, encoding a T-cell receptor recognizing the HLA-A2/gp100 complex, into T-cells24. Antigen-specific T-cell activation is assessed by expression of CD69 (early T-cell activation marker), proliferation assays and cytokine production. In this way, the T-cell stimulating capacities of the generated synthetic DCs can be easily tested.

Example 8: Streptavidin and αCD3 PLGA Microparticles Preparation

Microparticles (MPs) with streptavidin and αCD3 coated were prepared using PLGA (lactide:glycolide molar ratio 48:52 to 52:48) obtained from Boehringer Ingelheim (Resomer RG 502 H, Ingelheim, Germany). Microparticles (MPs) were prepared using the w/o/w emulsion solvent evaporation-extraction method. In brief, 50 mg of PLGA was emulsified under sonication in 1 mL of methylene chloride for 60 seconds. This first emulsion was rapidly added to 1 mL of 1% polyvinyl alcohol/7% ethyl acetate in distilled water. This solution was added to 200 mL of 0.3%

PVA/7% of ethyl acetate in distilled water and stirred overnight to evaporate ethyl acetate. Next, the MPs are rinsed three times with distilled water through centrifugation at 3000 g at 4° C. Finally, the MPs were lyophilized.

Carboxyl groups on the surface of the MPs (10 mg) were activated by re-suspending the MPs in 1 mL isotonic 0.1 M MES saline buffer pH 5.5, and then reacting them with EDAC (10 equiv.) and NHS (10 equiv.) for one hour. The MPs were then centrifuged to remove excess EDAC/NHS and the water-soluble isourea byproduct. Activated MPs were resuspended in 1 mL PBS buffer and reacted with 2 mg of streptavidin for 24 hours. The streptavidin-coated MPs were centrifuged and washed with PBS buffer to remove any unbound streptavidin. Next, the αCD3 was introduced for incubation for one hour at room temperature. The αCD3 excess was separated by centrifugation at 25000 g for 30 minutes, and then washed four times with PBS. The presence of surface antibodies on the MPs was confirmed by staining the MPs with goat anti-human secondary antibodies, followed by analysis on a FACS CALIBUR™ flow cytometer using CellQuest software (BD Biosciences, USA). The amount of antibodies on the MPs was determined by Coomassie Plus Protein Assay Reagent (Pierce).

Example 9: Isolation Peripheral Blood Leucocytes

Peripheral blood leucocytes were isolated from blood using Ficoll density gradient isolation. Isolated cells were taken up in RPMI 1640 medium containing 10% fetal calf serum. Cells suspension was diluted with RPMI 1640+10% fetal calf serum to 1 million cells per ml. One hundred thousand cells were seeded in a 96-well plate and the indicated stimulants added. All stimulations were performed in triplicate. The concentration of the stimulants were normalized to the concentration of the CD3 monoclonal antibody. For the controls without CD3 antibody, the same concentration of polymers was used as was used for the CD3-containing polymers. Cells were incubated overnight at 37° C. and 5% $CO_2$. The plate was centrifuged at 1500 rpm for five minutes to pellet all cells and supernatant was collected. The concentration of IFNγ was determined using Human IFNγ Colorimetric ELISA (Pierce:EHIFNG) according to the instructions of the manufacturer.

The invention claimed is:

1. A method for contacting a T-cell with a major histocompatibility complex (MHC) protein/antigen complex, the method comprising:
   contacting the T-cell with filamentous structures comprising
      an oligo(alkylene glycol) functionalized polyisocyanopeptide homopolymer backbone to which is attached one or more copies of the MHC protein/antigen complex and
      at least one T-cell co-stimulatory factor;
   wherein at least one MHC protein/antigen complex is attached to a terminal end of the oligo(alkylene glycol) functionalized polyisocyanopeptide homopolymer backbone.

2. The method according to claim 1, wherein the oligo(alkylene glycol) functionalized polyisocyanopeptide homopolymer has been obtained through polymerization of isocyanide monomers that have been derived from amino acids and/or peptides.

3. The method according to claim 1, wherein the filamentous structure either contains functional groups to increase its water solubility and/or has been functionalized to increase its water solubility.

4. The method according to claim 1, wherein the filamentous structure contains PEG groups to increase its water solubility and/or has been functionalized with PEG groups to increase its water solubility.

5. The method according to claim 1, wherein the filamentous structure further comprises at least one antigen complexed with at least one complex or molecule able to present an antigen to a T-cell, such that the filamentous structure is able to present the at least one antigen to the T-cell.

6. The method according to claim 1, wherein the antigen is selected from the group consisting of tumor antigens, tumor-associated antigens and anti-tumor peptides.

7. The method according to claim 5, wherein the at least one complex or molecule able to present an antigen to a T-cell is at least one CD1d molecule.

8. The method according to claim 1, wherein the antigen is a lipid or glycolipid antigen.

9. The method according to claim 1, wherein the at least one co-stimulatory factor is selected from the group consisting of B7.1, B7.2, CD2, CD27, 41BB, and CD40.

10. A method for contacting a T-cell in vivo with a major histocompatibility complex (MHC) protein/antigen complex, the method comprising:
    contacting a T-cell in vivo with a filamentous structure comprising
       an oligo(alkylene glycol) functionalized polyisocyanopeptide homopolymer backbone to which is attached multiple copies of the MHC protein/antigen complex and
       at least one T-cell co-stimulatory factor;
    wherein at least one copy of the MHC protein/antigen complex is attached to a terminal end of the oligo(alkylene glycol) functionalized polyisocyanopeptide homopolymer backbone.

11. The method according to claim 10,
    wherein the oligo(alkylene glycol) functionalized polyisocyanopeptide homopolymer has been obtained through polymerization of isocyanide monomers that have been derived from amino acids and/or peptides.

12. The method according to claim 10, wherein the filamentous structure contains PEG groups to increase its water solubility and/or has been functionalized with PEG groups to increase its water solubility.

13. The method according to claim 10, wherein the filamentous structure further comprises at least one antigen complexed with at least one complex or molecule able to present an antigen to a T-cell, such that the filamentous structure is able to present the at least one antigen to the T-cell.

14. The method according to claim 10,
    wherein the antigen is selected from the group consisting of tumor antigens, tumor-associated antigens and anti-tumor peptides.

15. The method according to claim 13,
    wherein the at least one complex or molecule able to present an antigen to a T-cell is at least one CD1d molecule.

16. The method according to claim 10,
    wherein the antigen is a lipid or glycolipid antigen.

17. The method according to claim 10, wherein the filamentous structure either contains functional groups to increase its water solubility and/or has been functionalized to increase its water solubility.

18. The method according to claim 10, wherein the at least one co-stimulatory factor is selected from the group consisting of B7.1, B7.2, CD2, CD27, 4-1BB, and CD40.

* * * * *